United States Patent
Veiga Fernandes et al.

(10) Patent No.: US 9,821,026 B2
(45) Date of Patent: Nov. 21, 2017

(54) USE OF RET AGONIST MOLECULES FOR HAEMATOPOIETIC STEM CELL EXPANSION PROTOCOLS AND TRANSPLANTATION THERAPY AND A RET AGONIST KIT

(71) Applicant: Instituto de Medicina Molecular, Lisbon (PT)

(72) Inventors: Jose Henrique Veiga Fernandes, Oeiras (PT); Diogo Da Fonseca Pereira, Lisbon (PT); Silvia Moura Arroz Nobre Madeira, Lisbon (PT)

(73) Assignee: INSTITUTO DE MEDICINA MOLECULAR, Lisbon (PT)

( * ) Notice: Subject to any disclaimer, the term of this patent is extended or adjusted under 35 U.S.C. 154(b) by 0 days.

(21) Appl. No.: 14/410,980

(22) PCT Filed: Jun. 26, 2013

(86) PCT No.: PCT/IB2013/055261
§ 371 (c)(1),
(2) Date: Dec. 23, 2014

(87) PCT Pub. No.: WO2014/002038
PCT Pub. Date: Jan. 3, 2014

(65) Prior Publication Data
US 2015/0190467 A1 Jul. 9, 2015

(30) Foreign Application Priority Data

Jun. 28, 2012 (PT) ........................................ 106413

(51) Int. Cl.
*C12N 5/0789* (2010.01)
*A61K 38/18* (2006.01)
*A61K 35/28* (2015.01)
*A01K 67/027* (2006.01)

(52) U.S. Cl.
CPC .............. *A61K 38/18* (2013.01); *A61K 35/28* (2013.01); *C12N 5/0647* (2013.01); *A01K 67/0276* (2013.01); *A01K 2227/105* (2013.01); *A01K 2267/0381* (2013.01); *C12N 2501/13* (2013.01); *C12N 2501/727* (2013.01)

(58) Field of Classification Search
CPC ...... A61K 38/18; A61K 35/28; A61K 38/185; C12N 5/0647; C12N 2501/727; C12N 2501/13
See application file for complete search history.

(56) References Cited

U.S. PATENT DOCUMENTS

| | | | | |
|---|---|---|---|---|
| 6,232,449 B1* | 5/2001 | Johnson, Jr. | ......... | C07K 14/475 530/350 |
| 2004/0203142 A1* | 10/2004 | Rai | ...... | C12N 5/0647 435/368 |
| 2006/0265774 A1* | 11/2006 | Shinohara | .............. | C12N 5/061 800/24 |
| 2007/0041954 A1* | 2/2007 | Ichim | ..................... | A61K 35/44 424/93.7 |
| 2008/0241106 A1* | 10/2008 | Austen | ................. | A61K 38/185 424/93.7 |
| 2013/0230580 A1* | 9/2013 | Frenette | ................. | A61K 31/05 424/450 |

OTHER PUBLICATIONS

PROSPEC catalog 2009, pp. 7 and 10. downloaded from http://web.archive.org/web/20090528234203/http://www.prospecbio.com/ [Dec. 13, 2016 2:28:39 PM].*
Gattei et al., Blood 1997 89:2925-2937.*
Kubota, H. et al. (2004). Growth factors essential for self-renewal and expansion of mouse spermatogonial stem cells. *Proceedings of the National Academy of Sciences of the United States of America*, 101(47), 16489-16494.
Hofmann, M-C. (2008). Gdnf signaling pathways within the mammalian spermatogonial stem cell niche. *Molecular and Cellular Endocrinology*, 288(1-2), 95-103.
Ding, L. et al. (2012). Endothelial and perivascular cells maintain haematopoietic stem cells. *Nature*, 481(7382), 457-462.
International Search Report, dated Dec. 10, 2013 in connection with PCT International Application No. PCT/IB2013/055261, filed Jun. 26, 2013.
Written Opinion of the International Searching Authority, dated Dec. 10, 2013 in connection with PCT International Application No. PCT/IB2013/055261, filed Jun. 26, 2013.

* cited by examiner

*Primary Examiner* — Daniel C Gamett
(74) *Attorney, Agent, or Firm* — Lucas & Mercanti, LLP

(57) ABSTRACT

The present disclosure relates to the use of RET, a transmembrane tyrosine kinase receptor, agonist molecules for Haematopoietic Stem Cell (HSC) expansion protocols and HSC transplantation therapy.
RET signaling molecules are expressed by HSCs and Ret ablation leads to reduced HSC numbers. RET signals provide HSCs with critical Bcl2 and Bcl2l1 surviving cues, downstream of p38/MAP kinase and CREB activation. Accordingly, enforced expression of RET down-stream targets, Bcl2 or Bcl2l1, is sufficient to restore the activity of Ret null progenitors in vivo. Remarkably, activation of RET improves HSC survival or maintenance and in vivo transplantation efficiency, thus opening new horizons to the usage of RET agonist in HSC expansion and transplantation protocols.
Additionally, the present disclosure describes a kit comprising RET agonist molecules, to be used in HSC expansion protocols and transplantation therapy.

2 Claims, 19 Drawing Sheets

USE OF RET AGONIST MOLECULES FOR HAEMATOPOIETIC STEM CELL EXPANSION PROTOCOLS AND TRANSPLANTATION THERAPY AND A RET AGONIST KIT

CROSS-REFERENCE TO RELATED APPLICATIONS

This application is a §371 national stage of PCT International Application No. PCT/IB2013/055261, filed Jun. 26, 2013, claiming priority of Portuguese Patent Application No. 106413, filed Jun. 28, 2012, the contents of each of which are hereby incorporated by reference in their entirety.

FIELD OF INVENTION

The present disclosure relates to the use of RET agonist molecules in haematopoietic stem cell expansion protocols and transplantation therapy.

BACKGROUND OF THE INVENTION

For many blood cell malignancies such as certain types of leukaemia and multiple myeloma, haematopoietic stem cell (HSC) transplantation is an important therapeutic option. Furthermore, these cells are extensively used in research and in the development of urgently needed treatments for other diseases, including HIV and multiple sclerosis. The use of HSCs is however severely constrained by the limited expansion of these cells: Current cell culturing techniques result in insufficient quality and quantity of stem cells.

Many studies have tried to stimulate HSC expansion by experimenting with cytokine cocktails in cell culture media. Although these combinations of growth factors are able to increase the amount of HSCs, this happens at the cost of cell maturation: many of the cells in the final culture have lost their stem cell properties, in other words have lost their 'stemness', and thus their use for treatment and R&D. This hampers treatment outcomes and R&D activities which also become excessively expensive and inefficient.

Beyond a doubt, improving HSC expansion has a huge societal benefit: HSC transplantation will be cheaper and applicable for many more patients. The cost reduction is of particular interest since, according to a recent report of the Agency for Health Care Research and Quality, HSC transplantation has generated the most rapid increase in total hospital costs over the last decade. Of particular interest is the use technology for the expansion of HSCs from umbilical cord blood (UCB), a highly promising novel source of HSCs. Unfortunately, still 90% of patients referred for UCB transplantation are ineligible due to the limited number of stem cells available in a typical UCB unit.

The present disclosure for the expansion of these cells could provide a solution for this unmet medical need. Moreover, the improved availability of HSCs will drive research in stem cell biology and the development of novel treatment options for diseases such as HIV and multiple sclerosis.

Besides societal benefits there is also a significant commercial opportunity. US based stem cell research accounted for US $820 million in expenditures in 2005, with 10% (US $82 million) allocated for consumables such as media and culture suppliers. Spending on stem cell research is expected to reach US $2 billion by 2015 with approximately 20% (about US $400 million) allocated for consumables [Bioinformatics, 2009]. Multinational pharmaceutical companies increasingly turn to the development of stem cell therapies which indicates the presence of significant opportunities in this emerging market [Datamonitor, 2011].

The present invention intends to disclose the role of RET during haematopoiesis, leading to the discovery that neurotrophic factors have a strong beneficial effect on HSC survival, function and expansion.

SUMMARY OF THE INVENTION

The present invention relates to the use of tyrosine kinase receptor (RET) agonist molecules as regulators of stem cell maintenance, expansion or transplantation.

A preferred embodiment of the present invention describes the use of RET agonist selected from the group comprising glial cell-line derived neurotrophic factor, neurturin, artemin, persephin or mixtures thereof.

In another embodiment of the present invention, the stem cell are haematopoietic stem cells which maintain their stemness.

A preferred embodiment of the present invention describes the use of RET agonist molecules for the treatment of any condition susceptible of being improved or prevented by haematopoietic stem cells transplantation therapy.

It is also an objective of the present invention to describe a kit for haematopoietic stem cells maintenance or expansion or transplantation, comprising a cell culture media of the said cells with at least one RET agonists, selected from the group comprising glial cell-line derived neurotrophic factor, neurturin, artemin, persephin or mixtures thereof.

It is also an objective of the present invention to describe the use of the referred kit in protocols of maintenance, expansion or transplantation of haematopoietic stem cells.

GENERAL DESCRIPTION OF THE INVENTION

Hematopoietic stem cell transplantation is currently used to treat a variety of haematopoietic malignancies such as leukaemia. However, transplantation still remains limited by small HSC numbers and poor engraftment. Identification of new targets that improve HSC function is a key goal in transfusion medicine and cancer therapy. In the present disclosure it is identified such type of molecule: neuronal growth factors signaling through RET regulate HSC function and promote HSC survival. Accordingly, HSC treatment with neuronal growth factors was very successful in HSC transplantation and expansion protocols, with no significant side effects in normal blood generation.

The present disclosure opens new perspectives to the usage of RET agonists in HSC industrial expansion protocols and HSC transplantation therapy. Astonishingly, and in contrast to the current thinking, it is also disclosed that haematopoietic and neuronal stem cells maintain their fitness via similar signals. More specifically, the neurotrophic factor receptor RET is critical to HSC survival and function, thus RET signalling molecules are expressed by HSCs and Ret ablation leads to reduced HSC numbers. Despite normal differentiation potential, RET null progenitors exhibit loss of in vivo stress response and reconstitution potential, being rapidly exhausted. Strikingly, RET signals provide HSCs with critical Bcl2 and Bcl2l1 surviving cues, downstream of p38/MAP kinase and CREB activation. Accordingly, enforced expression of RET down-stream targets, Bcl2 or Bcl2l1, is sufficient to restore the activity of Ret null progenitors in vivo.

Remarkably, activation of RET results in improved HSC survival and in vivo transplantation efficiency, thus opening new horizons to the usage of RET agonist in HSC expansion and transplantation protocols.

Finally, the present embodiment shows that RET is an essential cell-autonomous regulator of HSCs function, revealing neurotrophic factors as novel components of the HSC microenvironment.

(mean±s.e.); t-test P=0.003. Vav1iCre $Ret^{WT/fl}$n=10; Vav1iCre $Ret^{null/fl}$n=7. Two tailed t-test P value is indicated. Error bars show s.e.

Figure 9:
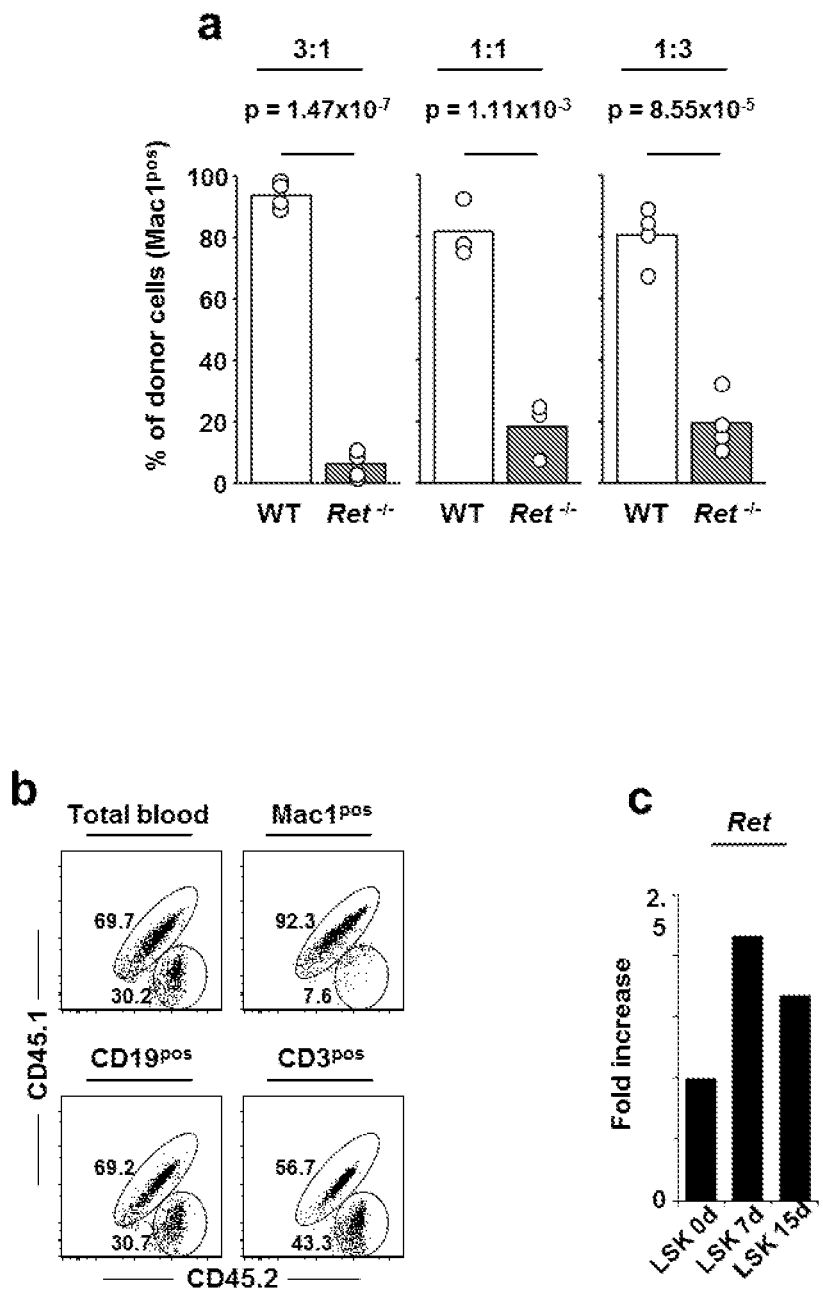

FIG. 9. Ret deficient LSKs have reduced fitness at different transplantation ratios and Ret expression increases after LSK transplantation. a. Competitive transplantation assay was performed with $Lin^{neg}cKit^{pos}$ from E14.5 $Ret^{-/-}$ CD45.2 and WT CD45.1/CD45.2 in different proportions. Percentage of $Mac1^{pos}$ cells post-secondary transplantation. Left: co-injected $1.5 \times 10^5$ WT CD45.1/CD45.2 and $0.5 \times 10^5 Ret^{-/-}$ CD45.2 (3:1). Middle: co-injected $1 \times 10^5$ WT CD45.1/CD45.2 and $1 \times 10^5$ $Ret^{-/-}$ CD45.2 (1:1). Right: co-injected $0.5 \times 10^5$ WTCD45.1/CD45.2 and $1.5 \times 10^5 Ret^{-/-}$ CD45.2 (1:3). 3:1 n=4; 1:1 n=3; 1:3 n=4. b. Flow cytometry analysis of blood cells from 1:3 recipients at 8 weeks. c. E14.5 FL LSK cells were transplanted to lethally irradiated recipients. Transplanted LSK cells were purified at 7 and 15 days after transplant and analysed by quantitative RT-PCR. Two tailed t-test P values are indicated.

Figure 10:
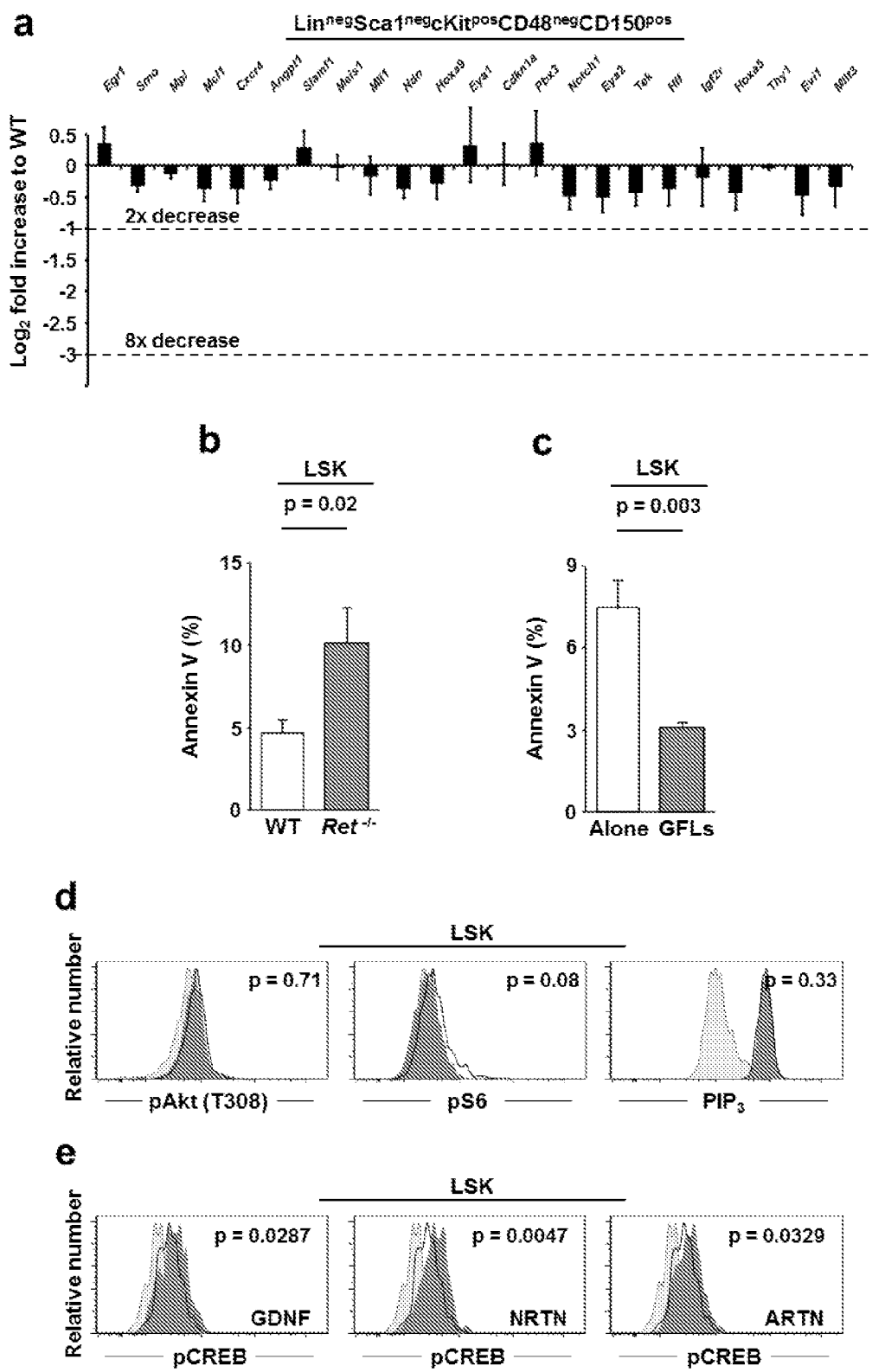

FIG. 10. RET signalling results in increased survival and CREB phosphorylation. a. Quantitative RT-PCR for FL E14.5 $Ret^{-/-}$ and WT HSCs. n=3. b. Percentage of $AnnexinV^{pos}$ LSK cells after culture. WT n=7, $Ret^{-/-}$ n=4. c. Percentage of $AnnexinV^{pos}$ LSK cells after culture. Alone n=7, GFLs n=4. d. Flow cytometry analysis E14.5 $Ret^{-/-}$ or WT littermate control LSK cells. WT n=6; $Ret^{-/-}$ n=6. e. Flow cytometry analysis of LSK cells in absence or presence of GDNF, NRTN or ARTN for 1 h. n=6. Two tailed t-test P value is indicated. Light grey: isotype control.

Figure 11:
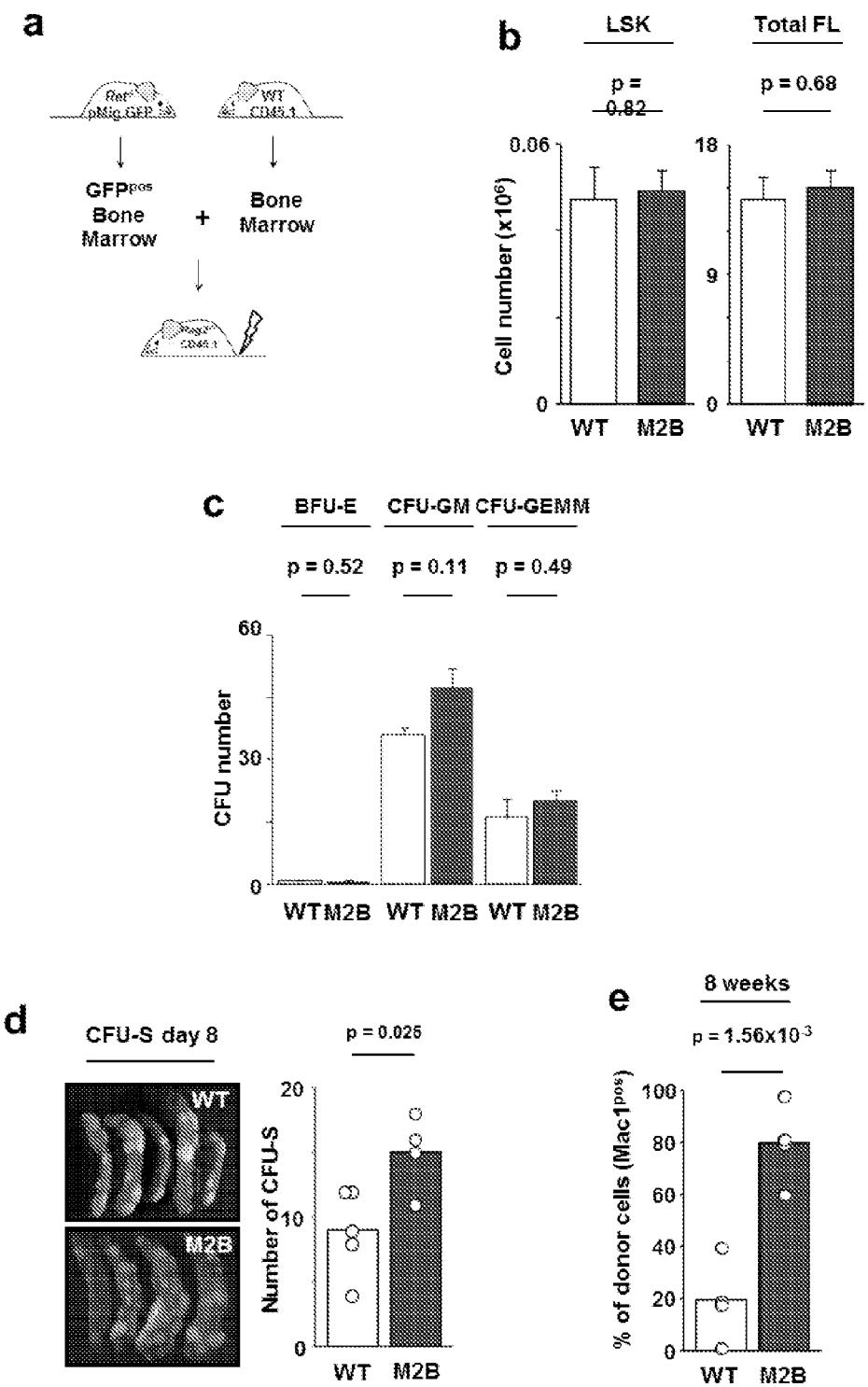
Figure 11:
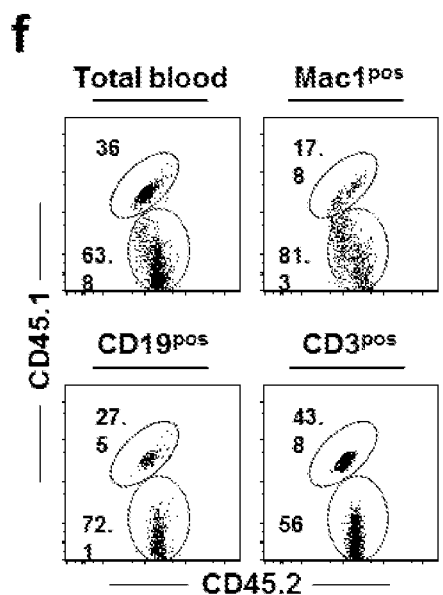
Figure 11:
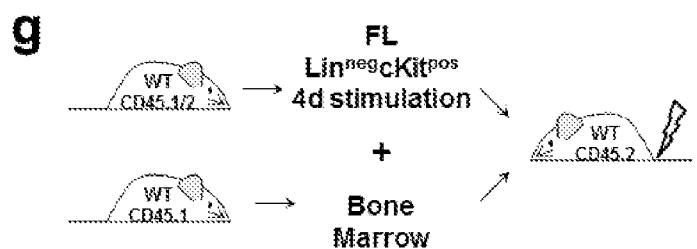

FIG. 11, 11'. Analysis of $Ret^{MEN2B}$ LSK differentiation and transplantation potential. a. Scheme of competitive transplantation rescue of Ret deficient progenitors. Relative to FIG. 4b-d. b. Number of LSK and total FL cells. WT n=10; $Ret^{MEN2B}$ n=15. c. Day 8 CFU colony numbers. WT n=3; $Ret^{MEN2B}$ n=3. d. Day 8 CFU-s. WT n=5; $Ret^{MEN2B}$ n=4. e. Competitive transplantation assay with $Ret^{MEN2B}$ CD45.2 and WT CD45.1/2. Percentage of $Mac1^{pos}$ cells post-secondary transplantation. n=4. f. Blood cell lineages from $Ret^{MEN2B}$ CD45.2 and WTCD45.1/2 origin 8 weeks post-transplantation. g. Scheme of competitive transplantation with GFLs treatment. Relative to FIG. 4e-g. Two tailed t-test P value is indicated. Error bars show s.e.

Figure 12:
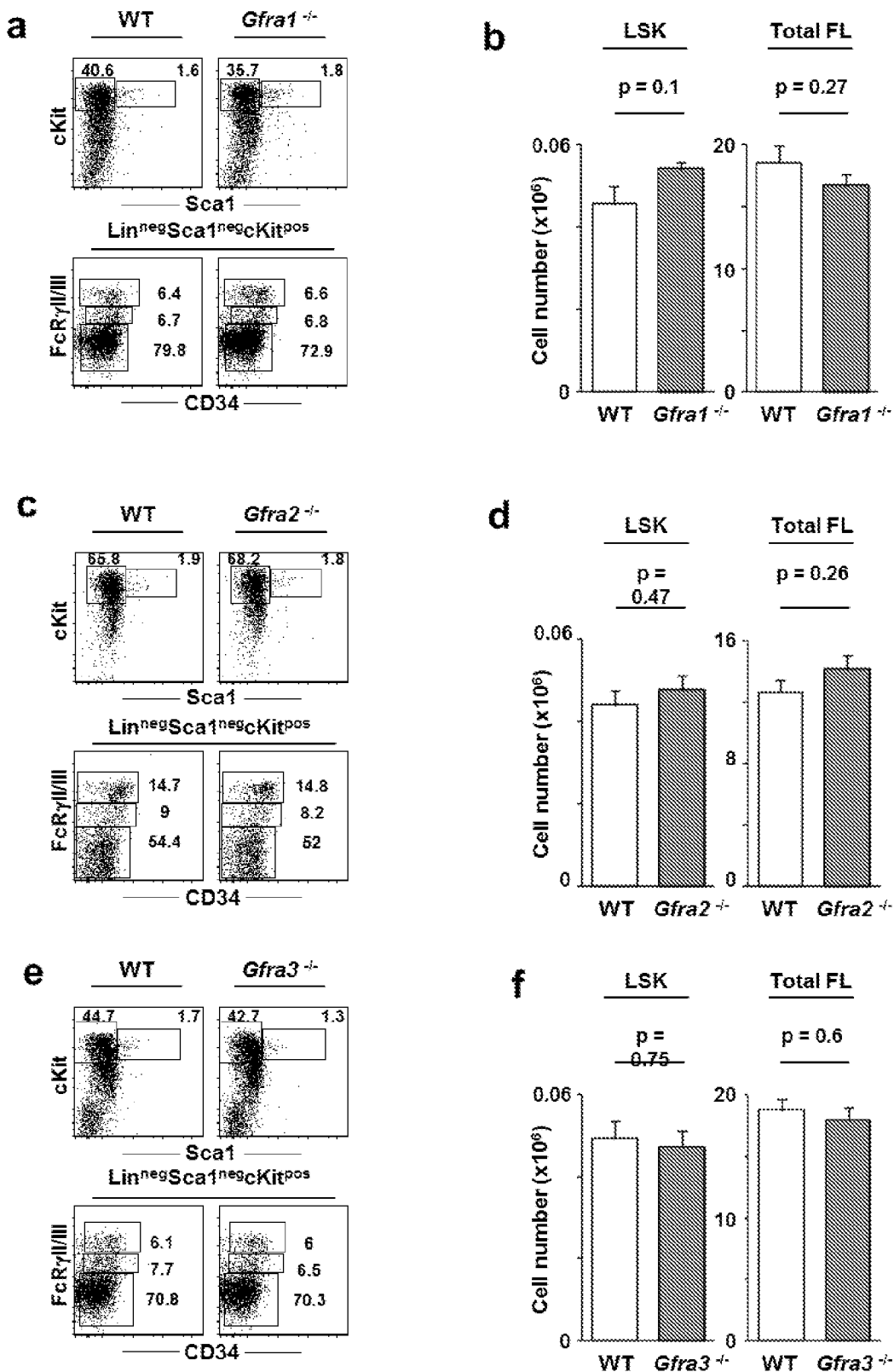

FIG. 12. Gfra deficient embryos have normal LSK cell numbers. a. Flow cytometry analysis of $E14.5Gfra1^{-/-}$ and WT littermate control LSKs (top) and MPs (bottom). b. Number of LSKs and total FL cells. WT n=9; $Gfra1^{-/-}$ n=10. c. Flow cytometry analysis of E14.5 $Gfra2^{-/-}$ and WT littermate control LSKs (top) and MPs (bottom). d. Number of LSKs and total FL cells. WT n=12; $Gfra2^{-/-}$ n=11. e. Flow cytometry analysis of $E14.5Gfra3^{-/-}$ and WT littermate control LSKs (top) and MPs (bottom). f. Number of LSKs and total FL cells. WT n=11; $Gfra3^{-/-}$ n=20. Two tailed t-test P value is indicated. Error bars show s.e.

Figure 13:
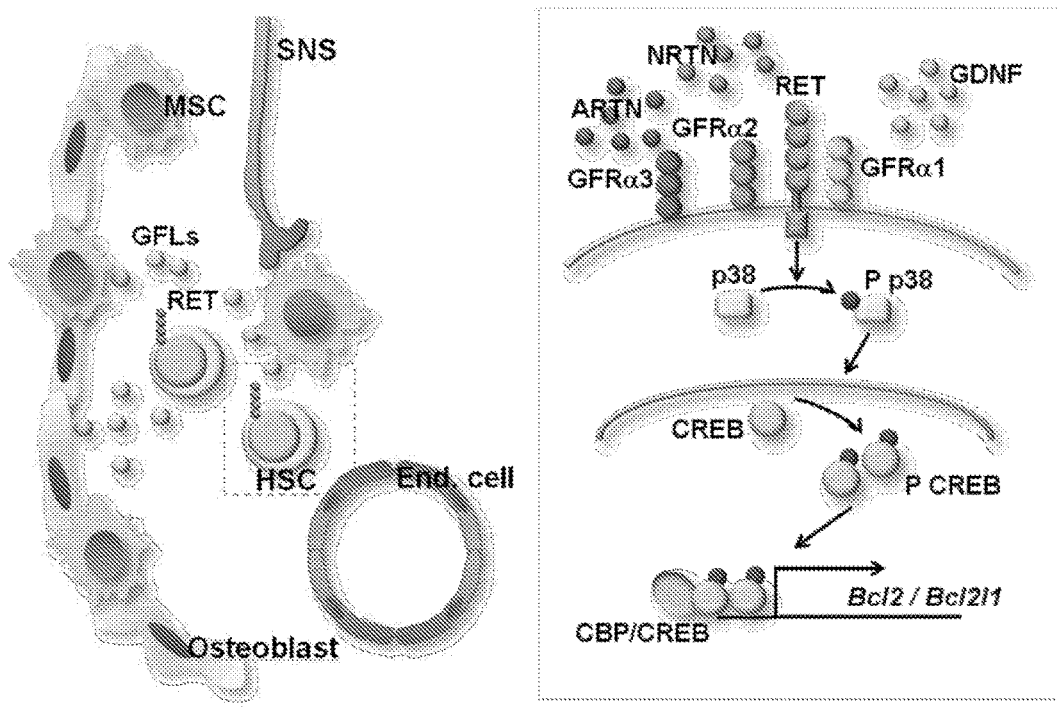

FIG. 13. Neuronal growth factors regulate HSC response to physiological demand. The neurotrophic factors GDNF, NRTN and ARTN are produced by cells in the HSC microenvironment and act directly on HSCs by binding to RET/GFRα heterodimers. Highlighted area: RET stimulation results p38/MAP kinase and CREB activation leading to Bcl2 and Bcl2l1 expression. Thus, RET signal provide HSCs with critical survival signals.

DETAILED DESCRIPTION OF THE INVENTION

Haematopoiesis starts during embryonic life, mainly in the Foetal Liver (FL), and is maintained throughout adulthood in the Bone Marrow (BM). Although HSCs are mostly quiescent in adults, they become proliferative upon physiological demand. Interestingly, autonomic nerves have been recently shown to actively participate in HSC niches raising the hypothesis that neurotrophic factors may regulate HSC function. The neuronal growth factor family includes the glial cell-line derived neurotrophic factor (GDNF) ligands (GFLs), which signal through the RET tyrosine kinase receptor and act mainly in the autonomous nervous system, kidney and mature lymphoid cells.

Figure 1:
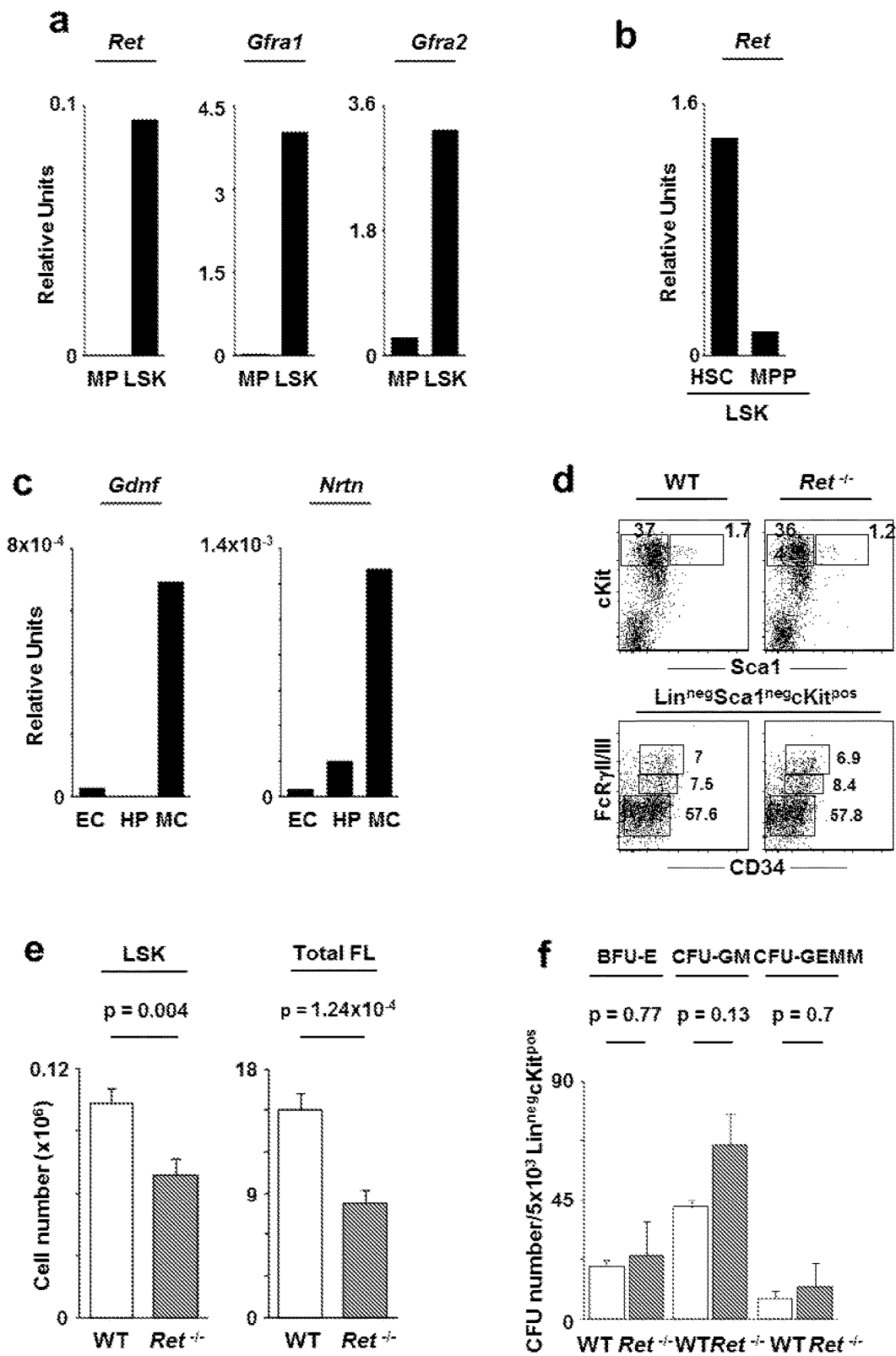
FIG. 1, 1'. Ret deficiency leads to reduced HSCs. a., b. FL E14.5 MP and LSK, HSCs and MPPs were analysed by quantitative RT-PCR. c. FL E14.5 TER119$^{neg}$CD45$^{neg}$CD31$^{pos}$ endothelial cells (EC), TER119$^{neg}$CD45$^{neg}$CD31$^{neg}$cKit$^{pos}$ICAM-1$^{neg}$ hepatocyte progenitor cells (HP) and TER119$^{neg}$CD45$^{neg}$CD31$^{neg}$cKit$^{neg}$ICAM-1$^{pos}$ mesenchymal cells (MC) were analysed by quantitative RT-PCR. d. Flow cytometry analysis of E14.5 Ret$^{-/-}$ and WT littermate control LSKs (top) and MPs (bottom). e. Number of LSKs and total FL cells. WT n=18; Ret$^{-/-}$ n=17. f. Day 8 CFU colony numbers. WT n=3; Ret$^{-/-}$ n=3. g. BrdU and Ki-67 in E14.5 LSK cells. h. Percentage of Ki-67$^{neg}$ LSKs (G0 cells). WT n=12; Ret$^{-/-}$ n=14. i. Number of E14.5 HSCs. WT n=20; Ret$^{-/-}$ n=18. j. Survival of VaviCre. Ret$^{null/fl}$ and littermate controls after 5-FU treatment. WT n=5; Ret$^{-/-}$ n=6. Two tailed t-test P values are indicated. Error bars show s.e.
Figure 1:
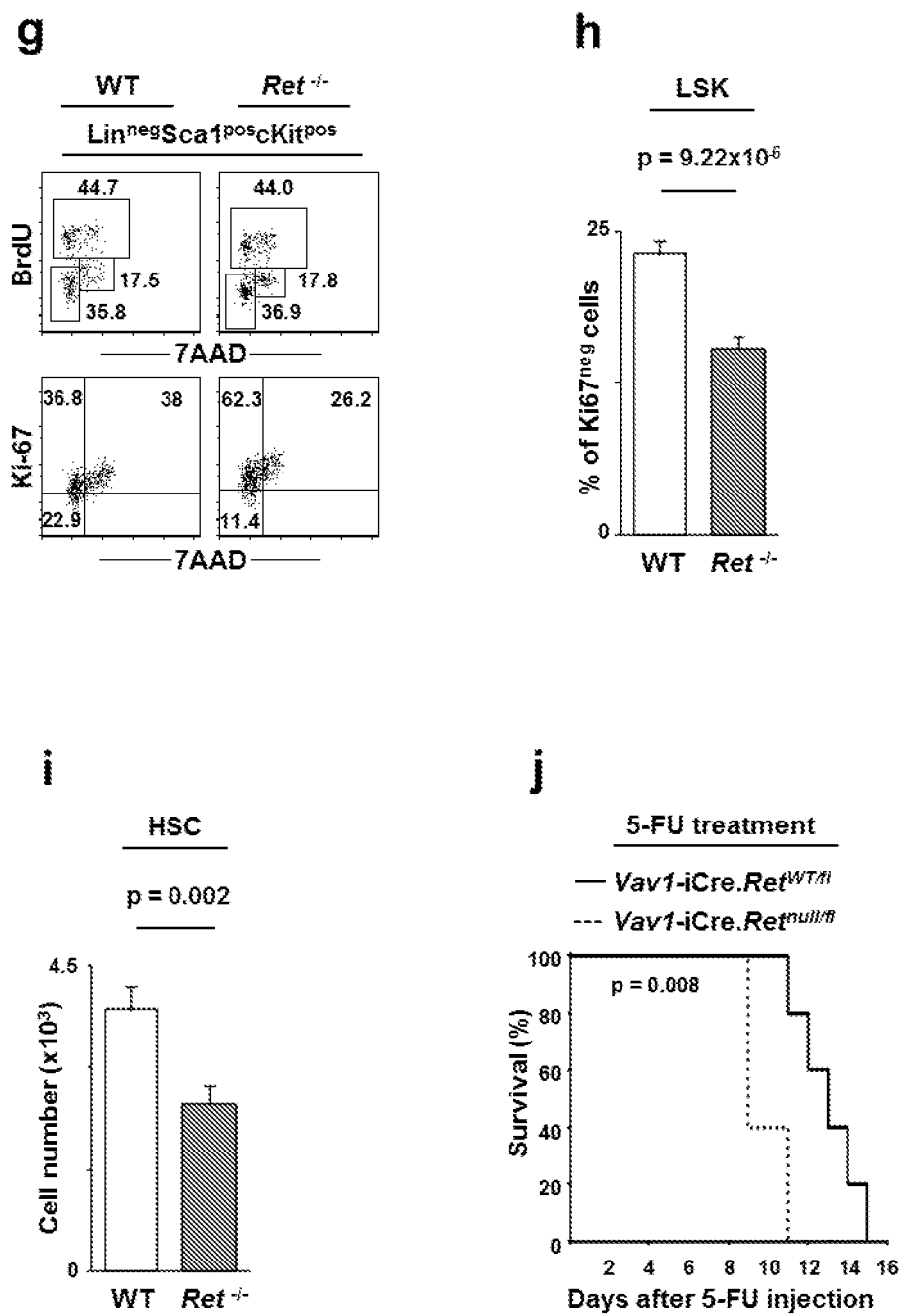
Figure 5:
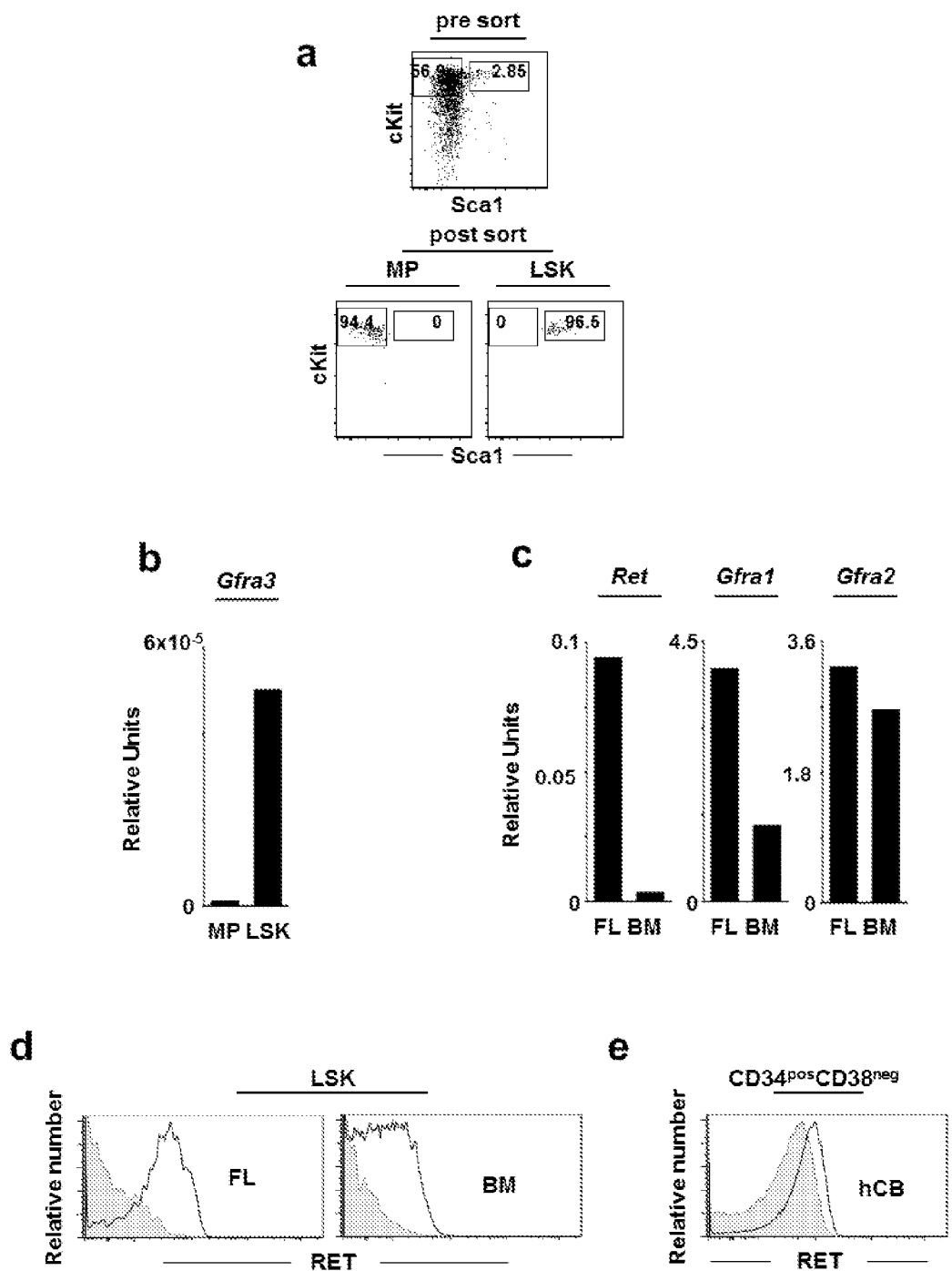
FIG. 5. Ret expression in haematopoietic progenitors. a. Purification strategy of Lin$^{neg}$Sca1$^{neg}$cKit$^{pos}$myeloid progenitors (MP) and Lin$^{neg}$Sca1$^{pos}$cKit$^{pos}$ (LSK) cells from E14.5 FL by flow cytometry. Top: pre sortgated on Lin$^{neg}$ cells. Bottom: purity of Lin$^{neg}$Sca1$^{neg}$cKit$^{pos}$ myeloid progenitors (left) and Lin$^{neg}$Sca1$^{pos}$cKit$^{pos}$cells (right) after sorting. b. FL E14.5 MP and LSK were analysed by quantitative RT-PCR. c. LSK cells from E14.5 FL and adult BM were analysed by quantitative RT-PCR. d. Flow cytometry analysis of E14.5 FL and adult BM LSK cells. e. Flow cytometry analysis of CD34$^{pos}$CD38$^{neg}$ cells from human cord blood (hCB). Lightgrey: isotype control.
Figure 6:
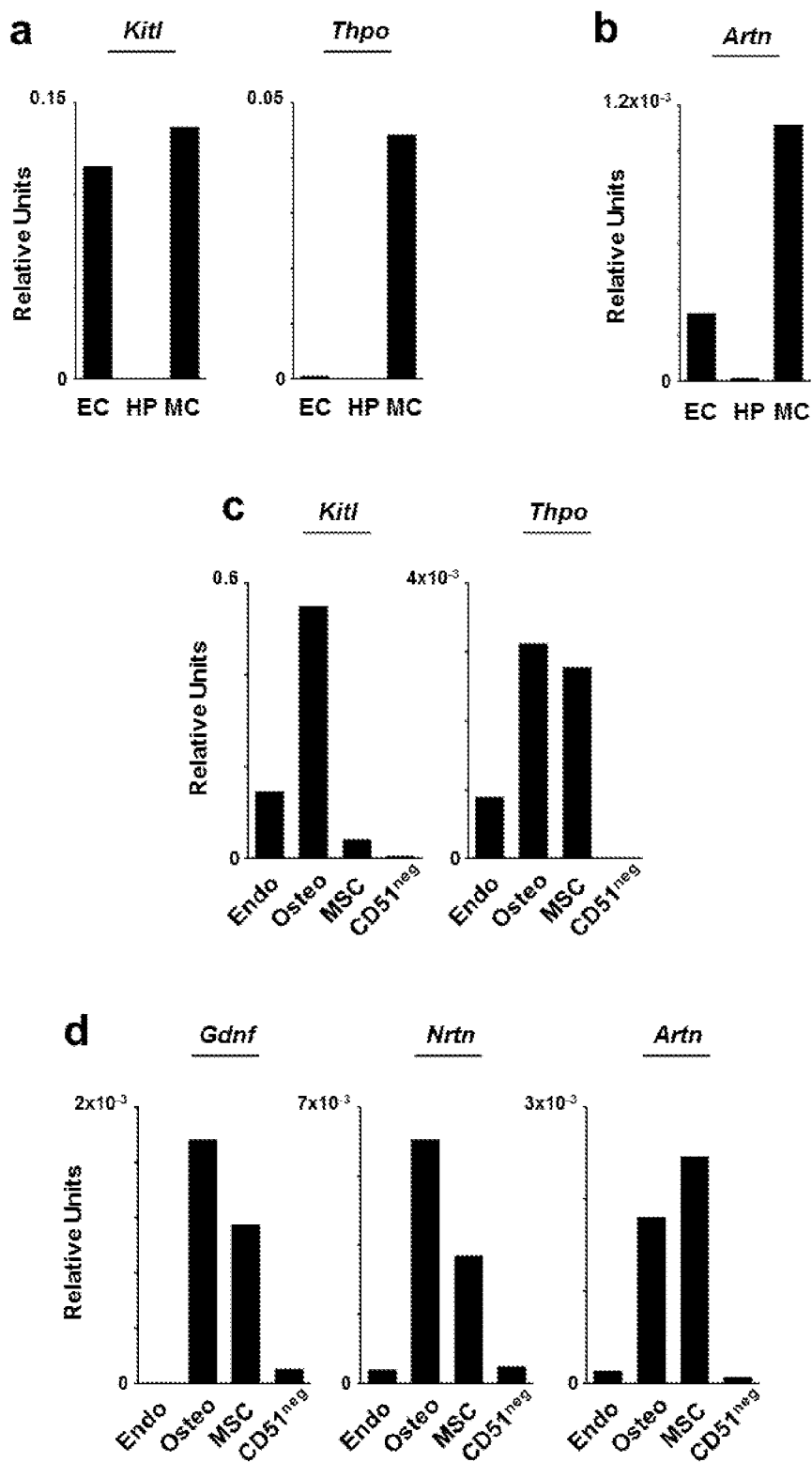
FIG. 6. Ret ligands are expressed in foetal and adult haematopoietic stem cell environment. a., b. E14.5 FL TER119$^{neg}$CD45$^{neg}$CD31$^{pos}$ endothelial cells (EC), TER119$^{neg}$CD45$^{neg}$CD31$^{neg}$cKit$^{pos}$ICAM-1$^{neg}$hepatocyte progenitor cells (HP) and TER119$^{neg}$CD45$^{neg}$CD31$^{neg}$cKit$^{neg}$ICAM-1$^{pos}$mesenchymal cells (MC) were analysed by quantitative RT-PCR. c., d. BM TER119$^{neg}$CD45$^{neg}$CD31$^{pos}$SCa1$^{pos}$ endothelial cells (Endo) TER119$^{neg}$CD45$^{neg}$CD31$^{neg}$SCa1$^{neg}$CD51$^{pos}$ osteoblasts (Osteo), TER119$^{neg}$CD45$^{neg}$CD31$^{neg}$Sca1$^{pos}$CD51$^{pos}$mesenchymal stem cells (MSC) and the remaining TER119$^{neg}$CD45$^{neg}$CD31$^{neg}$Sca1$^{neg}$CD51$^{neg}$ (CD51) cells were analysed by quantitative RT-PCR. Results are representative of three independent experiments.

To determine the role of GFLs in HSC biology, the expression of their canonical receptor RET in embryonic day 14.5 (E14.5) FL $Lin^{neg}Sca1^{pos}cKit^{pos}$ (LSK) cells was initially determined, a population highly enriched in HSCs. When compared to myeloid progenitors ($Lin^{neg}Sca1^{neg}cKit^{pos}$) (MP), LSKs expressed high levels of Ret and its co-receptors Gfra1, Gfra2, and Gfra3; this result was also confirmed in BM LSKs and human $CD34^{pos}CD38^{neg}$ cord blood progenitors (FIG. 1a; FIG. 5). Strikingly, Ret expression was restricted to $Lin^{neg}Sca1^{pos}cKit^{pos}CD150^{pos}CD48^{neg}$ haematopoietic stem cells (HSC), while multipotent progenitors ($Lin^{neg}Sca1^{pos}cKit^{pos}CD150^{neg}CD48^{pos}$ (MPPs)) expressed this gene poorly (FIG. 1b). Interestingly, FL mesenchymal cells and BM osteoblasts, which produce key factors to HSCs, such as Kit ligand and thrombopoietin, co-expressed the neurotrophic RET ligands GDNF, neurturin (NRTN) and artemin (ARTN), further suggesting an unexpected involvement of RET signalling in HSCs (FIG. 1c; FIG. 6).

Figure 7:
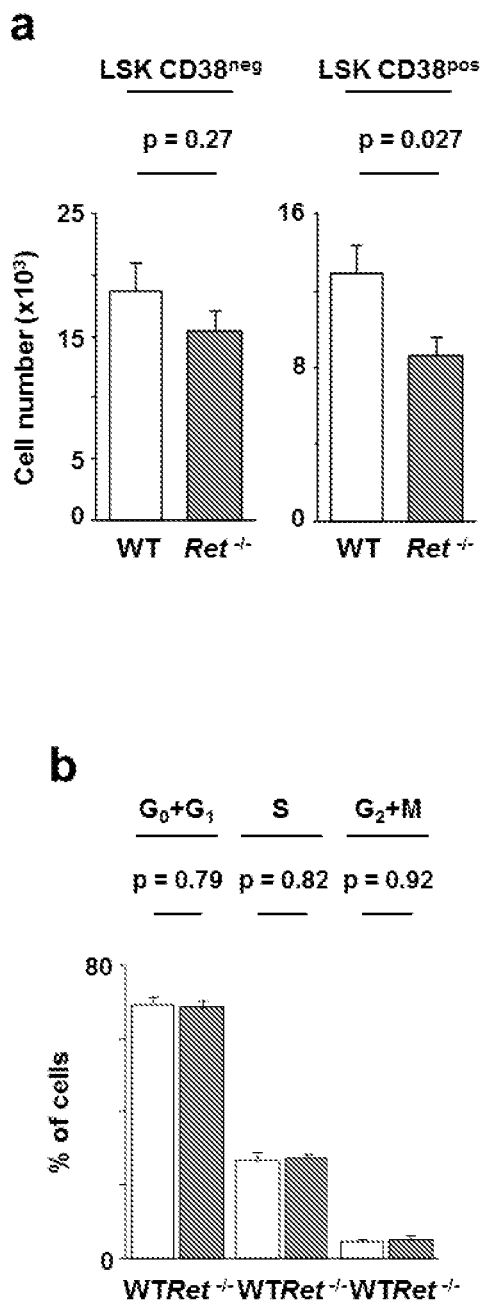
FIG. 7. Long-term reconstituting LSK cell numbers are affected by Ret deficiency. a. Number of E14.5ST-LSK (LSKCD38$^{neg}$) and LT-LSK (LSKCD38$^{pos}$) cells. WT n=12; Ret$^{-/-}$ n=11. b. Percentage of LSK cells inG0+G1, S or G2+M cell cycle phases according to DNA content (7AAD). WT n=7; Ret$^{-/-}$ n=6. Two tailed t-test Pvalue is indicated. Error bars show s.e.

To dissect this hypothesis, mice with a null mutation of $Ret^9$ were analysed. E14.5 Ret deficient progenitors were generated in similar proportions to their WT littermate controls (FIG. 1d). However, LSK numbers and total foetal liver cellularity were strongly reduced in $Ret^{-/-}$ embryos (FIG. 1e). Despite their reduced cell number, the differentiation potential of $Ret^{-/-}$LSKs was intact as revealed by normal numbers of methylcellulose colony-forming units (CFU) (FIG. 1f). Further dissection of LSK cells into short-term (ST-LSK) and long-term LSKs (LT-LSK) by CD38 expression, revealed a preferential reduction of Ret deficient LT-LSKs (FIG. 7a). This abnormal LSK population structure correlated with an altered cell cycle status of $Ret^{-/-}$LSK. Thus, despite similar G1/S/G2+M fractions (FIG. 7b), and turnover rate determined by BrdU incorporation (FIG. 1g), quiescent $Ki-67^{neg}$ $G_0$ phase LSKs were consistently reduced in $Ret^{-/-}$ animals (FIG. 1g-h). Accordingly, Ret deficiency resulted in decreased HSC numbers (FIG. 1i).

Figure 8:
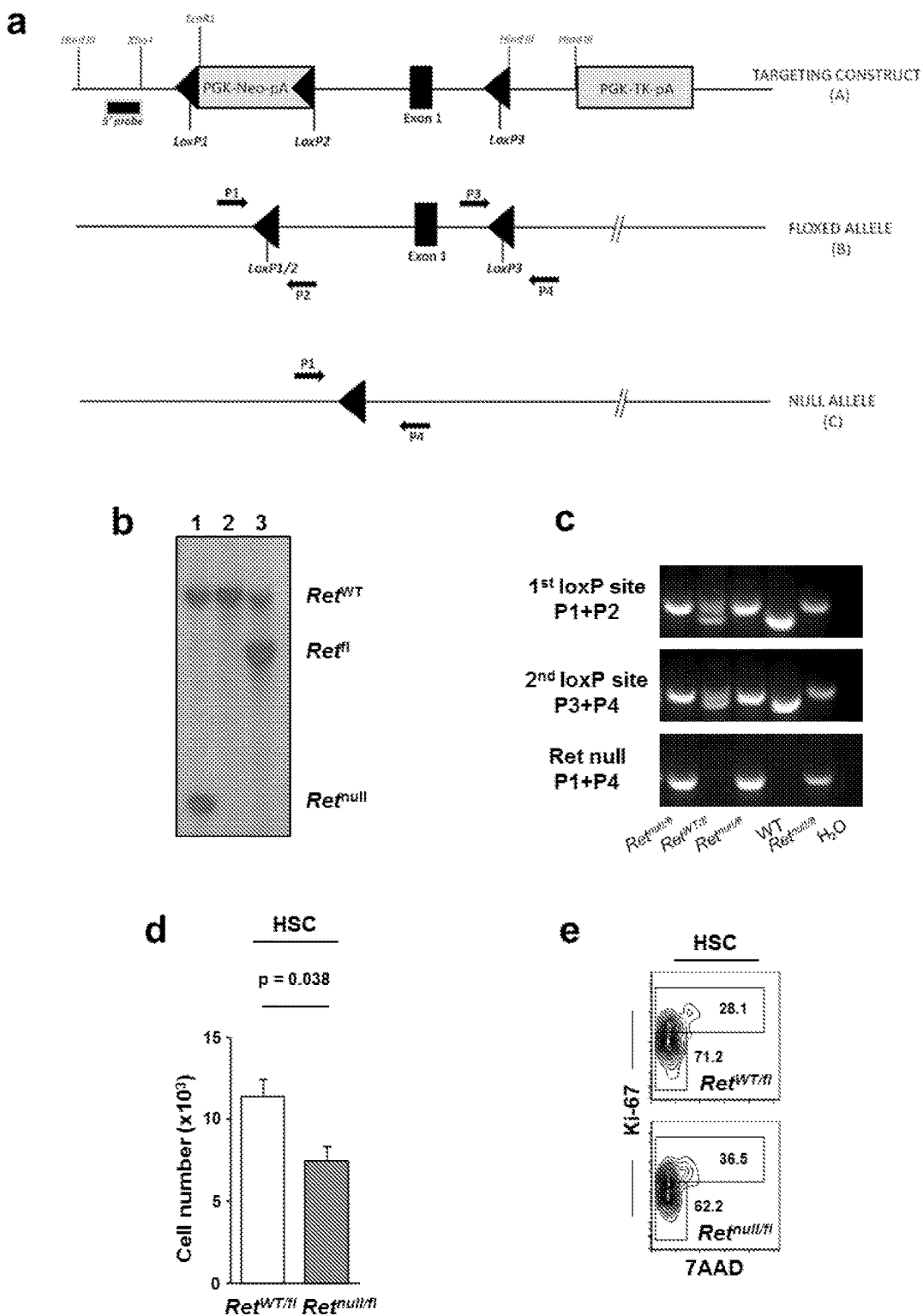
FIG. 8. Generation of Ret conditional knockout mice and analysis of BM haematopoietic stem cells. a. (A) The floxed Neomycin cassette was inserted ~4.5 kb upstream of exon 1 of mouse Ret locus, a third loxP(LoxP3) was introduced downstream of exon 1 and ~5 kb downstream the PGK-TK-pA cassette was inserted to aid negative selection. Targeted events were identified by Southern analysis of either Hind III digests of genomic DNA using the 5' external probe. (B) The floxed allele was identified by PCR and the primers P1/P2 were used to identify the loxP that remained after excision of the Neomycin cassette (PGK-Neo-PA), while the loxP3 was identified using primers P3/P4. The primer sequences are in the methods section. (C) To screen for the null allele, primers P1 and P4 were used. b. Southern-blot using HindIII digest and the 5' external probe. c. Genotyping results from a litter of mice obtained from a cRet131$^{WT/null}$×cRet131$^{fl/fl}$ breeding. In the loxP sites PCRs, upper band corresponds to the sequence with the loxP site and the lower band to the WT sequence. d. Numbers of BM HSCs. Vav1iCre Ret$^{WT/fl}$(Ret$^{WT/fl}$) n=5; Vav1iCre Ret$^{null/fl}$ (Ret$^{null/fl}$) n=4. e. Ki-67 in HSCs.Vav1iCre Ret$^{WT/fl}$=68.85±1.43; Vav1iCre Ret$^{null/fl}$=60.09±1.59

To test whether RET also affects adult HSCs we generated $Ret^{fl/fl}$mice that were bred to Vav1-iCre mice (FIG. 8). Strikingly, despite low levels of Ret expression in adult HSCs, Ret conditional ablation led to reduced quiescent HSCs numbers (FIG. 5, 8). These data suggested that RET may regulate HSC responses to physiological demands. In agreement, serial treatments with 5-fluorouracil (5-FU) revealed that $VavCre^{pos}/Ret^{null/fl}$ mice promptly died upon 5-FU treatment when compared to their $VavCre^{pos}/Ret^{wt/fl}$ littermate controls (FIG. 1j). Taken together, these results indicate that RET is required to the maintenance of a normal pool of quiescent HSCs and for haematopoietic stress responses.

Figure 2:
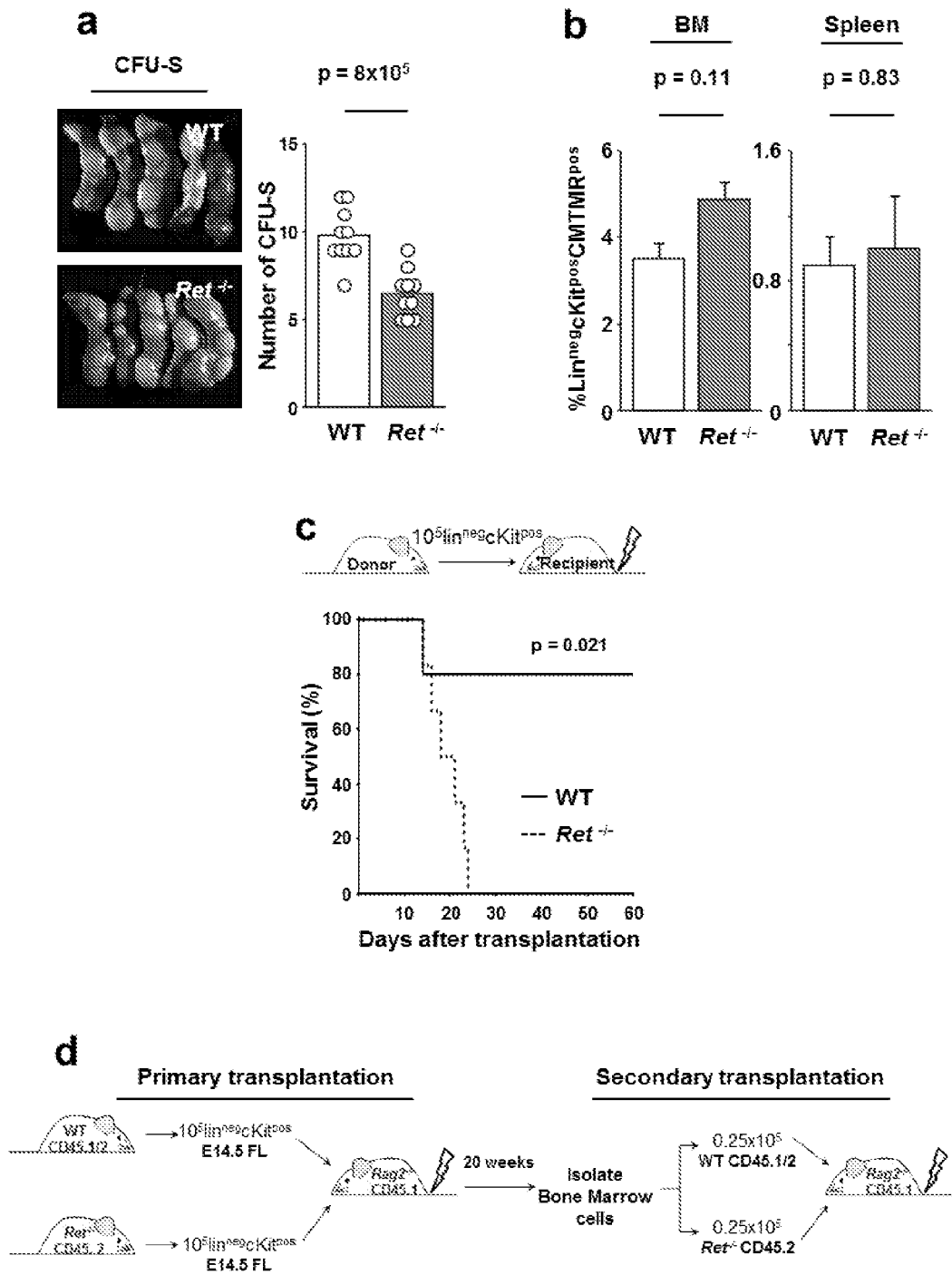
FIG. 2, 2'. Ret$^{-/-}$LSKs have poor in vivo reconstitution potential. a. Day 12CFU-s. WT n=10; Ret$^{-/-}$ n=10. b. Percentage of Lin$^{neg}$cKit$^{pos}$CMTMR$^{pos}$ cells in BM and spleen 20 h post-injection. WT n=3; Ret$^{-/-}$ n=3. c. Survival upon transplantation. P value for log rank test is indicated. WT n=5; Ret$^{-/-}$ n=6. d. Scheme of Primary and Secondary (red) transplantation. e. Percentage of Mac1$^{pos}$ cells after transplantation. WT n=8; Ret$^{-/-}$ n=8. f. Blood cell lineages 16 weeks post-transplantation. g. BM Lin$^{neg}$ and LSK cells at 16 weeks and percentage of BM LSK cells. WT n=4; Ret$^{-/-}$ n=4. h. Percentage of Mac1$^{pos}$ cells post-secondary transplantation. WT n=4; Ret$^{-/-}$ n=4. i. Blood cell lineages 16 weeks post-secondary transplantation. j. BM Lin$^{neg}$ and LSK cells at 16 weeks and percentage of BM LSK cells. WT n=4; Ret$^{-/-}$ n=4. Two tailed t-test P values are indicated. Error bars show s.e.
Figure 2:
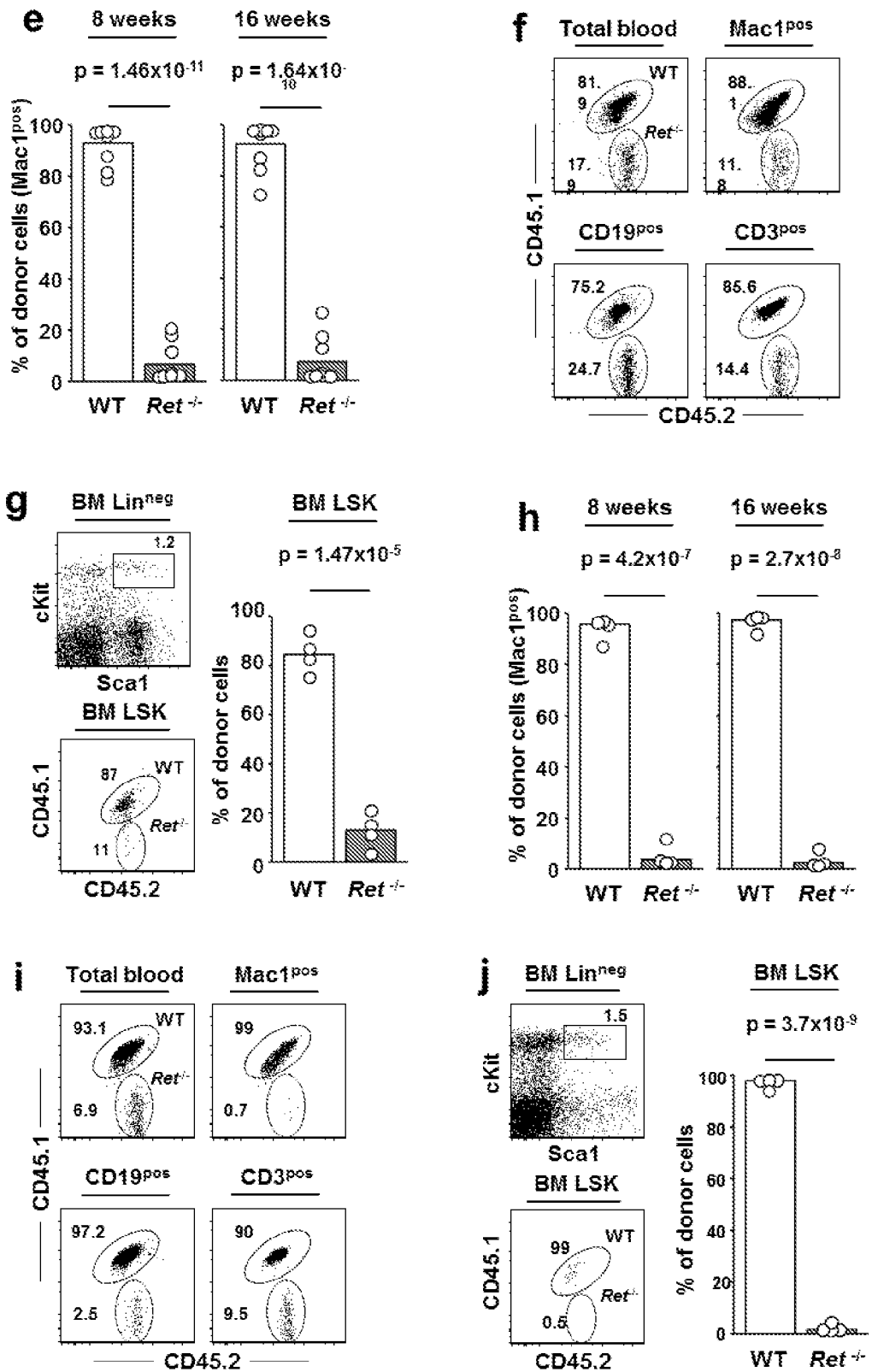

In the past, reduction of quiescent HSCs was correlated to impaired haematopoietic activity on a per cell basis. Accordingly, $Ret^{-/-}$ progenitors exhibited reduced CFU-s potential upon transplantation into lethally irradiated hosts (FIG. 2a). In order to assess whether Ret is required for long-term HSC transplantation we performed in vivo repopulation assays.

Strikingly, despite similar BM and Spleen colonising capacity (FIG. 2b), Ret deficient progenitors failed to rescue lethally irradiated mice, resulting in 100% host lethality (FIG. 2c). Since loss of reconstitution potential makes it impossible to evaluate the fate of Ret null progenitors, we performed competitive transplantation assays. Thus, foetal Ret$^{-/-}$ progenitors were co-transplanted with equal numbers of WT littermate progenitors that also provide supportive haematopoiesis and ensure host survival (FIG. 2d). Analysis of recipient mice revealed that Ret deficient progenitors lost their transplantation fitness across all blood cell lineages (FIG. 2e-f), a finding also confirmed when different donor cell ratios were transplanted (FIG. 9). These data suggested a role of RET in HSCs. Accordingly, BM analysis 4 months after transplantation showed minute frequencies of Ret deficient LSKs (FIG. 2g). Sequentially we performed highly sensitive secondary competitive transplantation assays with the same number of WT and Ret$^{-/-}$ BM cells isolated from primary recipients (FIG. 2d). We found minute frequencies of Ret$^{-/-}$ cells in blood (FIG. 2h-i), a defect already established in BM LSKs (FIG. 2j). Altogether, these findings demonstrate that RET is critically required for foetal and adult LSK function and transplantation activity, a finding also supported by Ret up-regulation upon LSK transplantation (FIG. 9c).

The marked deficiencies of RET null HSCs led us to investigated putative changes at the molecular level. Previous reports have identified a gene signature, associated with long term HSC activity. Strikingly, while most of those genes were not significantly modified, Bcl2 and Bcl2l1 were heavily reduced in Ret deficient LSKs and HSCs (FIG. 3a-b; FIG. 10a). The marked reduction of Bcl2 and Bcl2l1 anti-apoptotic genes suggested that RET could provide HSCs with critical survival signals. Accordingly, Ret null LSKs were highly susceptible to apoptosis, and GFLs efficiently increased LSK and HSC survival in culture conditions (FIG. 3c-e; FIG. 10b-c).

Figure 3:
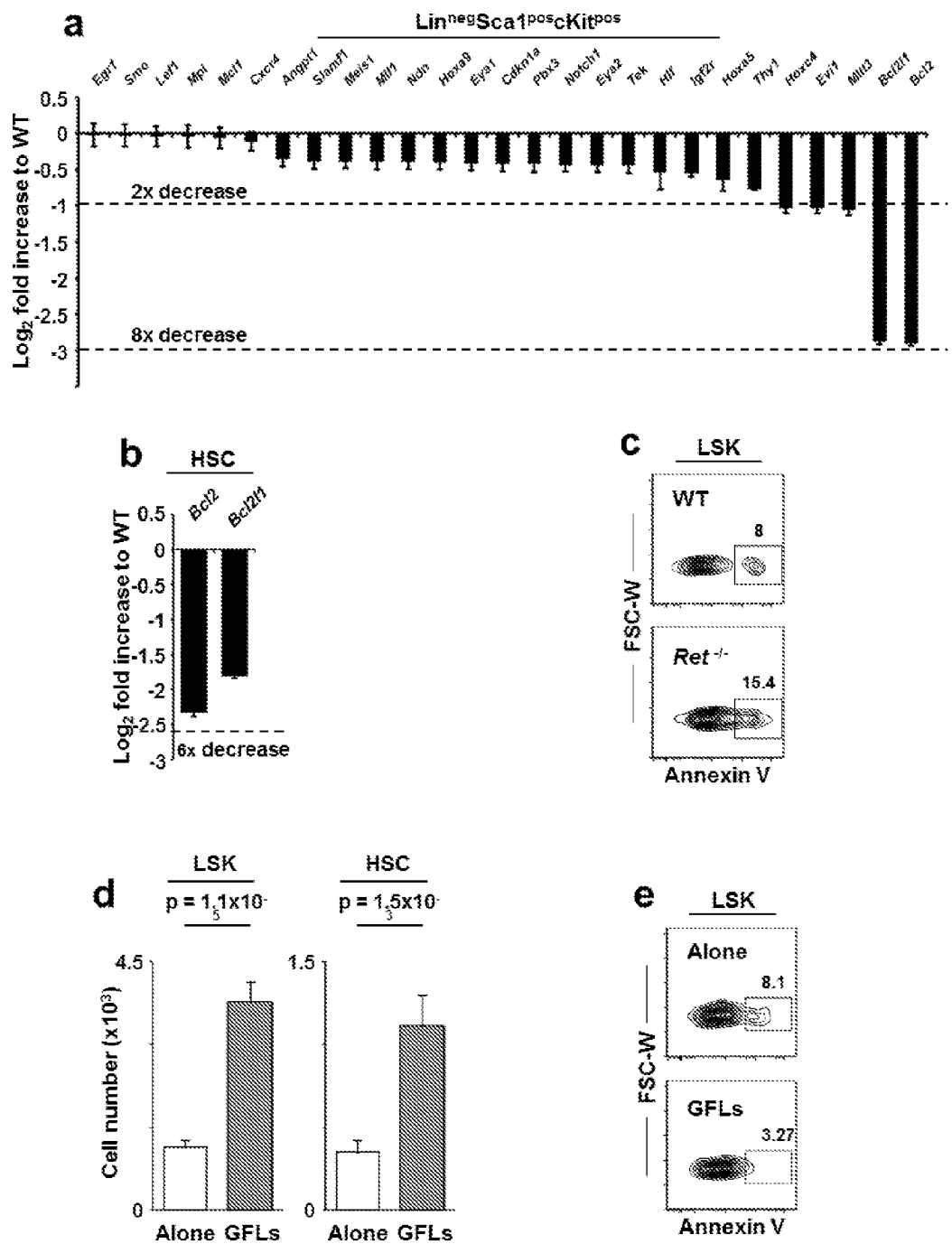
FIG. 3, 3', 3''. RET induces Bcl2/Bcl2l1 downstream of p38/MAP and CREB activation. a., b. Quantitative RT-PCR for FL E14.5 Ret$^{-/-}$ WT LSKs and HSCs. n=3. c. AnnexinV$^{pos}$ cells in cultured E14.5 LSK cells. WT n=7; Ret$^{-/-}$ n=4. d. Number of recovered LSKs and HSCs treated with GFLs for 4 days. n=12. e. AnnexinV$^{pos}$ cells in cultured LSK cells. Alone n=9; GFLs n=9. f. Flow cytometry of E14.5 Ret$^{-/-}$ and WT littermate control LSKs. WT n>8; Ret$^{-/-}$n>7. g. Flow cytometry analysis of LSK cells in the absence or presence of GFLs for 1 h. n>6. h. Bcl2 and Bcl2l1 expression upon GFL treatment. i. Flow cytometry analysis of LSKs cultured with GFLs (black line) or GFLs and the inhibitors SB 202190 (SB); PD98,059 (PD); or Akt1/2, Akt Inhibitor VIII (AktVIII) (solid grey). n>5. j. Bcl2 and Bcl2l1 expression upon GFL treatment and different inhibitors. k. Bcl2 and Bcl2l1 expression relative to untreated LSKs, upon GFL treatment or GFL+CBP–CREB interaction inhibitor (CREBinh). Two tailed t-test P values are indicated. Error bars show s.e. Light grey: isotype control.
Figure 3:
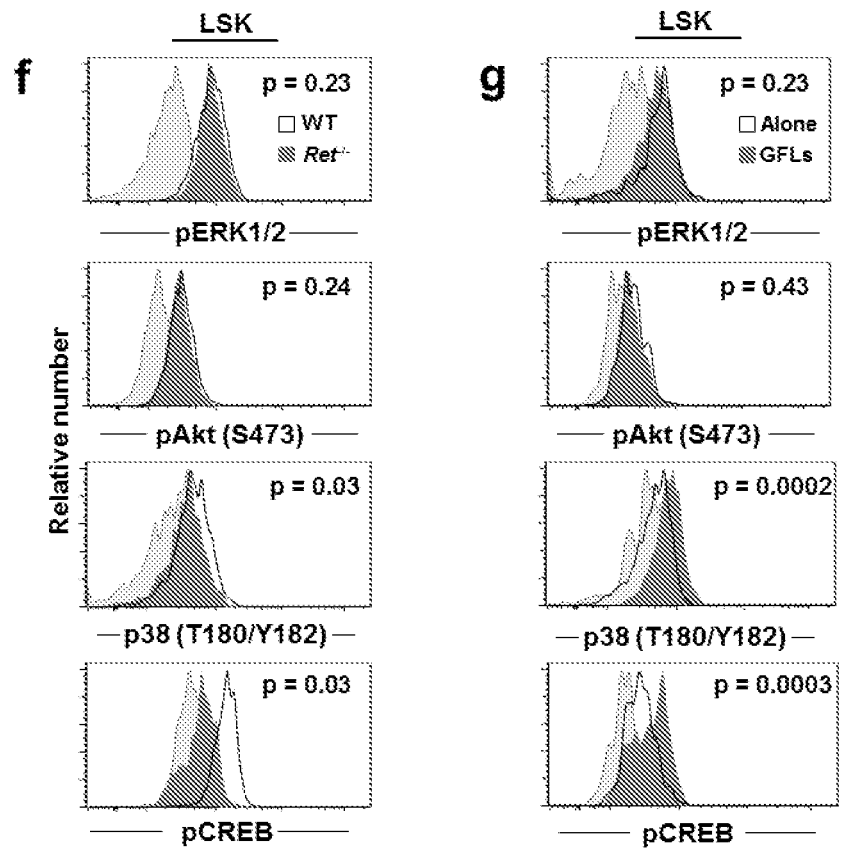
Figure 3:
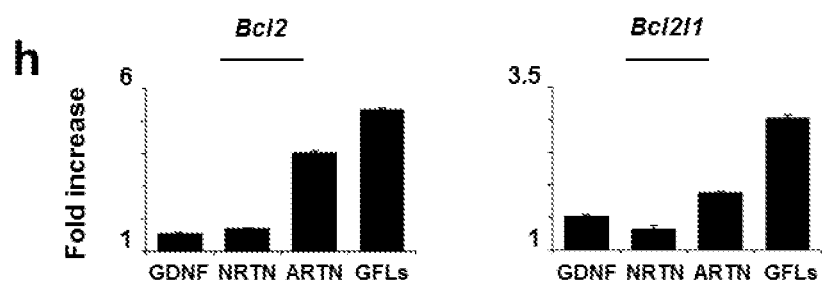
Figure 3:
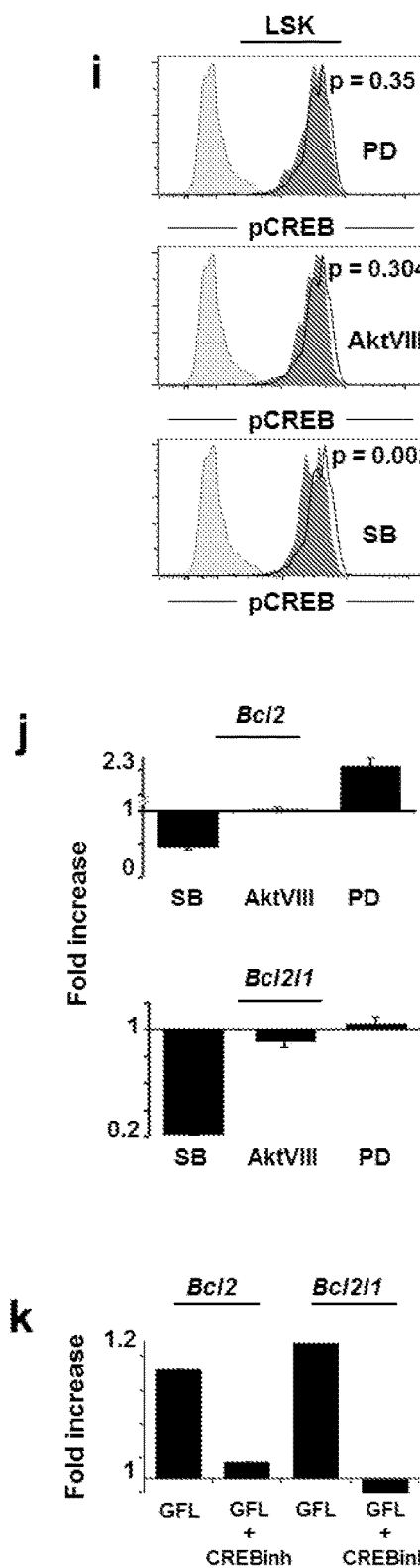

RET activation in neurons was shown to lead to ERK1/2, PI3K/Akt and p38/MAP kinase activation[6], while phosphorylation of the transcription factor CREB can induce Bcl2 gene family expression[18,19]. Analysis of p38/MAP kinase and CREB in Ret$^{-/-}$ LSKs revealed that these molecules were consistently hypo-phosphorylated, while ERK1/2 and PI3K/Akt activation was seemingly unperturbed when compared to their WT counterparts (FIG. 3f; FIG. 10d). Accordingly, GFL induced RET activation led to rapid p38/MAP kinase and CREB phosphorylation and increased Bcl2/Bcl2l1 expression by LSKs, while ERK1/2, PI3K/Akt phosphorylation was stable (FIG. 3g-h; FIG. 10e). Importantly, inhibition of p38/MAP kinase upon GFL activation led to impaired CREB phosphorylation and Bcl2/Bcl2l1 expression while inhibition of ERK1/2 and PI3K/Akt had no significant impact on these molecules (FIG. 3i-j). Finally, inhibition of CREB upon GFL activation resulted in decreased Bcl2/Bcl2l1 levels (FIG. 3k). Altogether, these data demonstrate that RET deficient progenitors express reduced Bcl2 and Bcl2l1, downstream of impaired p38/MAP kinase and CREB activation.

Figure 4:
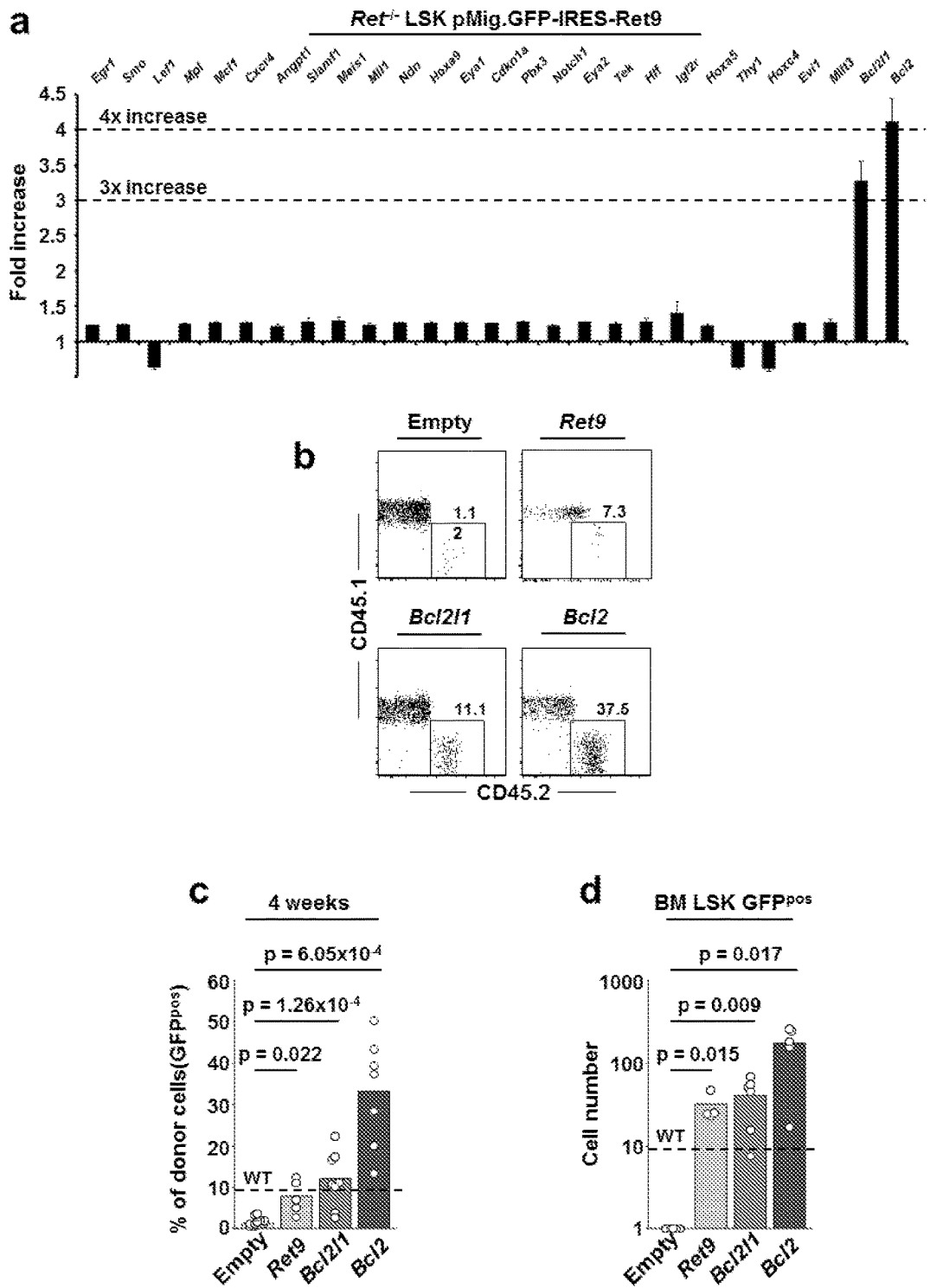
FIG. 4, 4'. Triggering of RET signalling improves transplantation activity. a. Quantitative RT-PCR. Fold increase ratio between Ret$^{-/-}$ pMig.GFP-IRES-Ret9 and empty vector. n=3. b. Flow cytometry analysis of Ret$^{-/-}$ blood cells at 4 weeks upon transduced cell transplantation. c. Percentage of CD45.2$^{pos}$GFP$^{pos}$ in the blood at 4 weeks post transplantation with Ret$^{-/-}$ progenitors transduced with pMig.GFP-IRES-Empty (Empty), pMig.GFP-IRES-Ret9 (Ret9), pMig.GFP-IRES-Bcl2l1 (Bcl2l1) orpMig.GFP-IRES-Bcl2 (Bcl2). Empty n=13; Ret9 n=5; Bcl2l1 n=8; Bcl2 n=7. d. Number of BM LSK cells transduced as indicated in FIG. 4b. Ret$^{-/-}$ Empty n=13; Ret9 n=4; Bcl2l1 n=6; Bcl2 n=5. e. Flow cytometry analysis of blood cells at 8 weeks upon transplantation. f. Percentage of CD45.2$^{pos}$ donor cells in Mac1$^{pos}$ cells from blood. Alone n=5; GFLs n=5. g. Percentage of BM CD45.2$^{pos}$ donor LSK and HSC cells, 12 weeks upon transplantation. Alone n=5; GFLs n=5. Two tailed t-test P values are indicated.
Figure 4:
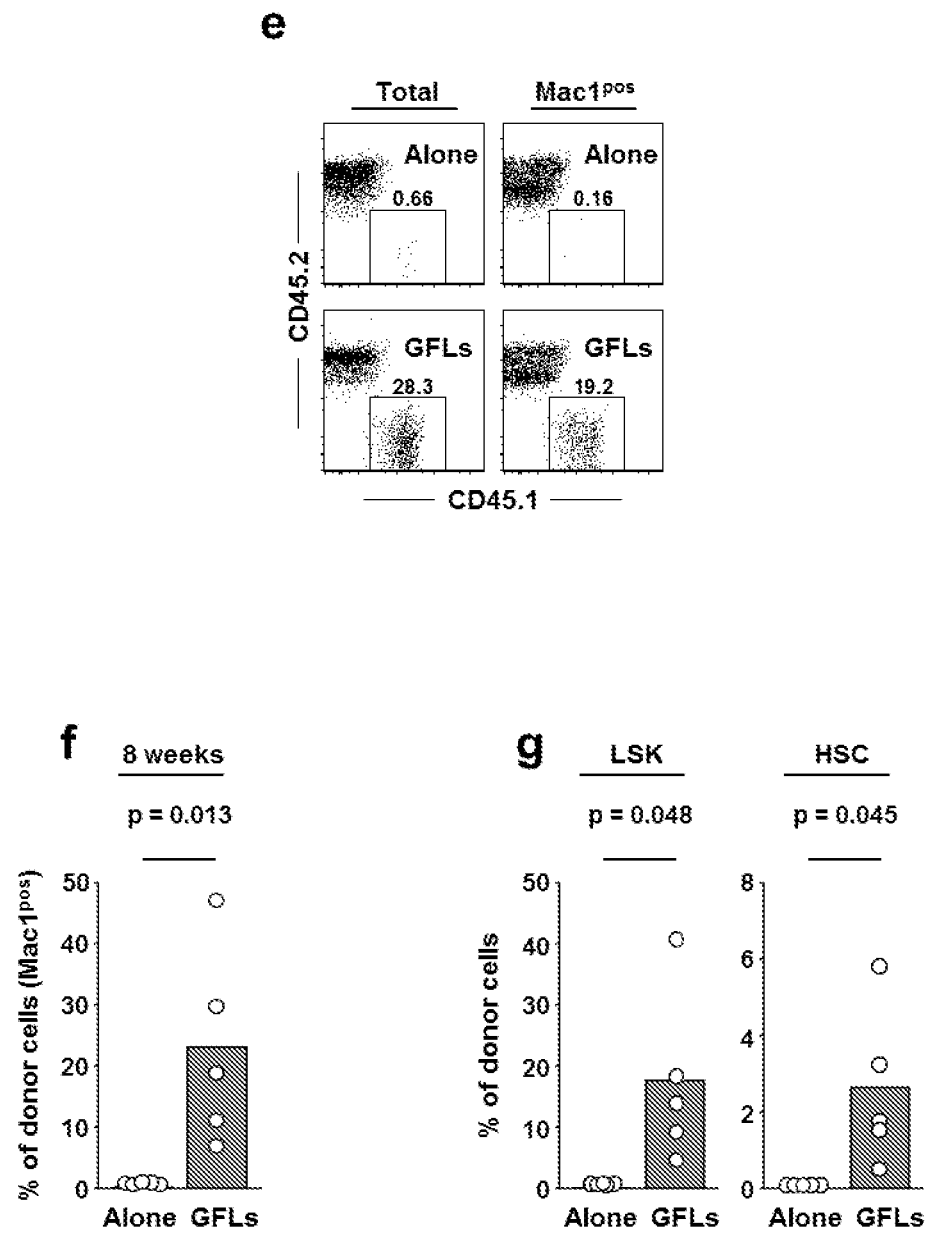

The aberrant molecular signature of Ret deficient HSCs, suggested that the minute levels of Bcl2 and Bcl2l1 were responsible for the observed LSK unfitness. Using retroviral transductions we found that Bcl2 and Bcl2l1 expression levels were quickly restored in Ret$^{-/-}$ LSKs transduced with WT Ret, while other signature genes were unperturbed by this immediate rescue of RET function (FIG. 4a). Thus, in order to test whether Ret$^{-/-}$ progenitor fitness could be restored by enforced expression of Ret it was performed a competitive transplantation assays with Ret deficient progenitors transduced with pMig.Ret9.IRES.GFP or pMig.Empty.IRES.GFP retro-virus together with a competitive/radio-protective dose of CD45.1 BM (FIG. 11a). Restoration of RET expression fully rescued Ret$^{-/-}$ progenitors transplantation (FIG. 4b-d). Strikingly, enforced expression of RET down-stream targets, Bcl2 or Bcl2l1, was sufficient to recover the engraftment of Ret null LSKs (FIG. 4b-d).

Altogether, these data suggest that RET signals might be used to improve blood cell transplantation. To directly test this hypothesis, initially we used Ret$^{MEN2B}$ mice, which have improved ligand-dependent RET activation[20]. Early haematopoietic progenitors in these animals exhibited a remarkable increased CFU-s activity and reconstitution potential. However, no difference was observed when comparing embryonic LSK numbers and downstream haematopoietic progenitors between Ret$^{MEN2B}$ and wild type mice (FIG. 11b-f). Hence, positive modulation of RET-signalling was clearly beneficial in transplantation without compromising steady state haematopoiesis. Further evidence that RET signalling axes promote HSC in vivo fitness was provided by transplantation of GFL pre-treated progenitors. E14.5 LSKs were treated with GFLs or medium alone and were transplanted with competitor CD45.1 BM (FIG. 11g). While untreated progenitors engrafted poorly in these conditions; GFL treated progenitors had strikingly increased transplantation fitness and HSC engraftment (FIG. 4e-g).

Our results reveal that RET signalling is a crucial novel pathway regulating foetal and adult HSC activity by providing critical surviving signals through BCL2 family members. Although no appreciable HSC survival deficiencies were reported in Bcl2 deficient mice, it is possible that haematopoietic stress conditions could reveal such deficits[21]. Alternatively, Bcl2 and Bcl2l1 may have redundant roles in HSCs, an idea supported by our data demonstrating that Bcl2l1 or Bcl2 are independently sufficient to fully rescue Ret deficient HSC function (FIG. 4b-d).

Haematopoietic progenitors express multiple RET co-receptors and actively respond to their respective ligands (FIG. 1a; FIG. 3g-h; FIG. 10). Contrary to nervous cells, HSCs might use GFLs in a versatile and redundant manner since analysis of RET co-receptors single knockouts revealed normal LSK numbers (FIG. 12). In agreement with this concept, it was recently shown that Lymphoid Tissue initiator cells can respond redundantly to all RET ligands. The data, here presented, indicates that absence of neurotrophic factor cues leads to impaired HSC survival and possible recruitment of quiescent LT-HSCs resulting in a pronounced deficiency of HSC transplantation in vivo. Accordingly, activation of RET results in increased Bcl2/Bcl2l1 expression, improved HSC survival and in vivo transplantation efficiency. Thus, RET controls HSC responses to physiological proliferative demands (FIG. 13). These results and the expression of RET in human CD34$^{pos}$CD38$^{neg}$ cord blood progenitors open new horizons for testing the usage of GFLs in human haematopoietic stem cell expansion and transplantation therapy.

Finally, the present embodiment supports a neural regulation of haematopoiesis. Previous work has revealed that nervous cells can modulate HSC function indirectly. However, herewith it is revealed that HSCs are direct targets of neurotrophic factors, suggesting that haematopoietic and neuronal stem cells require similar survival signals. Whether HSCs can also control autonomic nervous functions through neurotrophic factor consumption remains an elusive aspect. However, the presence of neurotrophic factors in the HSC environment paves the way to further studies connecting haematopoiesis and neural function regulation.

Methods

Mice: C57BL/6J (CD45.2 and CD45.1), Rag1$^{-/-}$ (CD45.2 and CD45.1)[29], Vav1-iCre[11], Gfra1$^{-/-}$[22], Gfra2$^{-/-}$[24], Gfra3$^{-/-}$[23], Ret$^{MEN2B}$[20] and Ret$^{-/-}$[9] were on a C57BL/6J genetic background. All mice strains were bred and maintained at IMM animal facility. Animal procedures were performed in accordance to national and institutional guidelines.

Generation of Ret Conditional Knockout Mice: To generate mice harbouring a conditional Ret knock-out allele we engineered a targeting construct that firstly, included the introduction of a floxed 2.1 kb, Neomycin resistance (Neo$^r$) cassette under the control of the phosphoglycerate kinase-1 (PGK) promoter and a polyA tail (pA). This cassette (PGK-NEO$^r$-pA) was inserted approximately 4.5 kb upstream at the Xho I site of the pBluescript KS (pBS KS) vector that carried approximately 13 kb of the 5' end of mouse Ret genomic locus flanking exon 1. The second modification included an insertion of a loxP ~2.5 kb downstream of exon 1, at the Hind III site in the intron between exons 1 and 2 of the mouse Ret locus. Finally, a viral thymidine kinase cassette (~3 kb) under the control of the PGK promoter (PGK-TK-pA) was inserted at the Hind III site ~5 kb downstream of the inserted LoxP site. To obtain homologous recombination, this targeting construct was linearised by Xho I, purified by gel elution and extraction using the Qiaquick gel extraction kit (Qiagen), prior to electroporation into 129SvJ-derived R1 ES cells grown on mouse embryonic fibroblast (MEF) feeder layers. Following double selection with 300 µg/ml Geneticin (G418, Invitrogen) and 2 µM Gancyclovir (Sigma), positive clones were identified by Southern blotting. Genomic DNA was digested with Hind III restriction enzymes and a 5' external probe of 500 bp was used to screen for positive clones. With the Hind III digest the WT and mutant alleles showed a band size of 16.5 kb and 6 kb respectively. Positive animals were subsequently crossed with transgenic mice expressing Vav1-iCre in order to delete the PGK-NEO$^r$-pA cassette. This recombination resulted in generating the floxed Ret mice wherein the two remaining LoxP sites were found flanking the first exon of the Ret locus, or the complete deletion of the first exon. These mice are further designated as Ret floxed (Ret$^{fl}$) and Ret null (Ret$^{null}$). Mice were further screened by PCR. Primer sequences were: P1: AAG CTC CCT CCT ACC GTG CT; P2: TGG GAT GAA CTC TGC CCA TT; P3: TGC TGC TCC ATA CAG ACA CA; P4: TAC ATG CTG TCT GCT CTC AG.

Colony-Forming Units Assays: 5×10$^3$ E14.5 Lin$^{neg}$cKit$^{pos}$ cells MACS purified (MiltenyiBiotec) from WT, Ret$^{-/-}$ or Ret$^{MEN2B}$ were cultured in M3434 (Stem Cell Technologies) and scored at day 8 to 10 by flow cytometry and microscope analysis. 3×10$^4$ E14.5 Lin$^{neg}$cKit$^{pos}$ cells were MACS (MiltenyiBiotec) purified from WT, Ret$^{-/-}$ or Ret$^{MEN2B}$ and were injected into lethally irradiated mice (9Gy) and CFUs scored after 8 to 10 days by flow cytometry and microscope analysis. Homing assays were done using E14.5 Lin$^{neg}$cKit$^{pos}$cells labelled with CMTMR, injected into lethally irradiated mice. Flow cytometry analysis was performed 20 h post-injection.

Transplantation experiments: For reconstitution experiments with foetal liver, 1×10$^5$ E14.5 Lin$^{neg}$cKit$^{pos}$ cells MACS purified from WT, Ret$^{-/-}$ or Ret$^{MEN2B}$ were injected alone or in direct competition (1:1 ratio) into lethally irradiated Rag1$^{-/-}$ CD45.1 mice. For the 3:1 ratio 1.5×10$^5$ WT CD45.1/CD45.2 cells were co-injected with 0.5×10$^5$ Ret$^{-/-}$ CD45.2 cells; for the 1:3 ratio 0.5×10$^5$ WT CD45.1/CD45.2 cells were co-injected with 1.5×10$^5$ Ret$^{-/-}$ CD45.2 cells. For secondary reconstitution experiments bone marrow 2.5×10$^5$ cells of each genotype were FACS sorted from primary recipients and injected in direct competition into lethally irradiated Rag1$^{-/-}$ CD45.1 mice.

Rescue of in vivo transplantation: E14.5 Lin$^{neg}$cKit$^{pos}$ WT or Ret$^{-/-}$ cells were transduced overnight with pMig.IRES-GFP retroviral vector containing Ret9, Bcl2 or Bcl2l1 and GFP$^{pos}$ cells were FACS sorted and injected into lethally irradiated mice. 6 to 8 weeks later transduced BM Lin$^{neg}$CD45.2$^{pos}$GFP$^{pos}$ were purified by flow cytometry and 10$^5$ cells were co-injected with a radio-protective dose 10$^5$ CD45.1 BM cells into lethally irradiated recipients.

Flow cytometry: Embryonic foetal livers were micro-dissected and homogenized in 70 µm cell strainers. Bone marrow cells were either collected by flushing or crushing bones. Cell suspensions were stained with: anti-CD117 (cKit) (2B8), anti-Ly-6A/E (Sca-1) (D7), anti-CD16/32 (FcRγII/III) (93), anti-CD3 (eBio500A2), anti-CD150 (mShad150), anti-CD48 (HM48-1), anti-CD19 (eBio1D3), anti-CD11b (M1/70), anti-Ly-6G (Gr-1) (RB6-8C5), anti-Ly79 (TER119), anti-NK1.1 (PK136), anti-CD11c (N418), anti-CD45.1 (A20), anti-CD45.2 (104), anti-CD54 (ICAM-1) (YN1/1.7.4), anti-CD34 (RAM34), anti-CD51 (RMV-7) and anti-CD41 (eBioMWReg30) from eBioscience; anti-CD38 (90), anti-CD3 (145-2C11), anti-CD34 (HM34) and anti-CD31 (390) from BioLegend; anti-Ly6C (HK1.4) from Abcam, Annexin V from BD Pharmingen. Lineage cocktail include anti-CD3, anti-CD19, anti-Ly-6G, anti-Ly6C, anti-Ly79, anti-NK1.1, anti-CD11c for embryonic foetal livers plus anti-CD11b for adult bone marrow cells. Human cord blood was enriched in CD34$^{pos}$ cells using CD34 MicroBead Kit (Miltenyi Biotec) after Histopaque separation (Sigma) and stained with anti-human CD34 (AC136) (Miltenyi Biotec) and anti-human CD38 (HIT2) (eBioscience). Samples were sorted on a FACSAria I or FACSAria III and analysed on a FACSCanto or LSRFortessa (BD). Flow cytometry data was analysed with FlowJo 8.8.7 software (Tree Star).

Cell cycle analysis and intracellular staining:

Intracellular stainings were done using BrdU Flow Kit and anti-BrdU (3D4), 7AAD, anti-Ki-67 (B56), anti-S6 (pS235/pS236) (N7-548) and anti-Akt (pT308) (JI-223.371) from BD Pharmingen, anti-human RET (132507) from R&D Systems, anti-PIP$_3$ (Z-P345) from Echelon Biosciences, anti-CREB (pS133) (87G3), anti-p38 (pT180/Y182) (28B10), anti-Akt (pS473) (D9E) and anti-ERK1/2 (pT202/pY204) (D13.14.4E) from Cell Signaling Technology.

in vitro culture of haematopoietic progenitors.

10$^6$ E14.5 WT Lin$^{neg}$cKit$^{pos}$ cells were cultured in DMEM and starved for 2 hours. To test CREB phosphorilation upon GFL stimulation Lin$^{neg}$cKit$^{pos}$cells were stimulated 1 hour with 500 ng/ml of each GFL and co-receptor. LSK cells were purified by flow cytometry and stimulated overnight with GFL/GFRα combinations in order to determine Bcl2 and Bcl2l1 expression levels. For inhibition experiments cells were incubated 2 hours prior GFLs stimulation, to test CREB phosphorilation, or during overnight stimulation with GFLs, to determine Bcl2 and Bcl2l1 expression levels, with SB 202190 and PD98,059 from Sigma-Aldrich or Akt1/2, Akt Inhibitor VIII and CBP-CREB Interaction Inhibitor from Calbiochem. Lin$^{neg}$cKit$^{pos}$ cells were stimulated with GFL/GFRα for 120 hours and 2.5×10$^5$ CD45.2$^{pos}$Lin$^{neg}$cKit$^{pos}$ cells were sequentially analysed by flow cytometry and transplanted into lethally irradiated hosts with a radio-protective dose 2.5×10$^5$ CD45.1 BM cells. To detect Annexin V, 4×10$^4$ E14.5 WT or Ret$^{-/-}$Lin$^{neg}$ckit$^{pos}$ cells per well were cultured overnight in DMEM alone or with GFL/GFRα. When analysed by flow cytometry haematopoietic progenitors were further stained with an LSK antibody cocktail.

Real-time PCR analysis: RNA was extracted from cell suspension using RNeasy Mini Kit or RNeasy Micro Kit (Qiagen). Real-time PCR for Ret, Gfra1, Gfra2 and Gfra3 were done as previously described [5,30]. Hprt1 was used as housekeeping gene. For TaqMan assays (Applied Biosystems) RNA was retro-transcribed using High Capacity RNA-to-cDNA Kit (Applied Biosystems), followed by a pre-amplification PCR using TaqMan PreAmp Master Mix (Applied Biosystems). TaqMan Gene Expression Master Mix (Applied Biosystems) was used in real-time PCR. TaqMan Gene Expression Assays bought from Applied Biosystems were the following: Gapdh Mm99999915_g1; Hprt1 Mm00446968_m1; Gusb Mm00446953_m1; Mpl Mm00440310_m1; Mcl1 Mm00725832_s1; Meis1 Mm00487664_m1; Angpt1 Mm00456503_m1; Eya1 Mm00438796_m1; Eya2 Mm00802562_m1; Egr1 Mm00656724_m1; Tek Mm00443243_m1; Slamf1 Mm00443316_m1; Lef1 Mm00550265_m1; Thy1 Mm00493681_m1; Mllt3 Mm00466169_m1; Hoxa5 Mm00439362_m1; Hoxa9 Mm00439364_m1; Hoxc4 Mm00442838_m1; Pbx3 Mm00479413_m1; Ndn Mm02524479_s1; Evi1 Mm00514814_m1; Mll1 Mm01179213_g1; Hlf Mm00723157_m1; Cxcr4 Mm01292123_m1; Smo Mm01162710_m1; Igf2r Mm00439576_m1; Cdkn1a Mm00432448_m1; Notch1 Mm00435249_m1; Kit1 Mm00442972_m1; Thpo Mm00437040_m1; Bcl2l1 Mm00437783_m1; Bcl2 Mm00477631_m1; persephin (PSPN) Mm00436009_g1; ARTN Mm00507845_m1; NRTN Mm03024002_m1; GDNF Mm00599849_m1; Ret Mm00436304_m1. For HSC signature gene arrays, gene expression levels were normalized to Gapdh, Hprt1 and Gusb. For Bcl2/Bcl2l1 expression after HSC stimulation and Ret expression levels after in vivo transfer gene expression levels were normalized to Gapdh and Hprt1.

Statistics. Statistical analysis was done using Microsoft Excel. Variance was analyzed using F-test. Student's t-test was performed on homocedastic populations and student's t-test with Welch correction was applied on samples with different variances. Kaplan-Meier survival curves were analyzed using a log rank test.

Results

RET agonist are naturally occurring proteins (ligands) that bind to the RET receptor with the help of an accessory protein (co-receptor). In humans and mice there are four ligands of RET, which are GDNF, NRTN, ARTN and PSPN, each of them having a specific co-receptor (respectively, GFRα1, GFRα2, GFRα3 and GFRα4). When RET agonist bind to RET receptor, the receptor becomes active and provides signals to the cells.

The following results demonstrate RET signalling function on HSC expansion and transplantation. That is the role of RET receptor in the development of the blood system in mice, particularly its impact on the function of the blood-forming stem cell, the haematopoietic stem cell (HSCs), using cultured assays and in vivo models.

Contrary to other molecular pathways used in current expansion protocols, such as KIT and FLT3, RET do not impact differentiation in vivo (FIG. 1d) or in vitro (FIG. 1f), but is regulates HSC numbers (FIG. 1e; FIG. 1i).

RET is critical for HSC survival as RET deficient cells express almost four times less pro-survival genes, Bcl2 and Bcl2l1 (FIG. 3b) and die in culture two times more than normal cells (FIG. 3c; FIG. 10b). Importantly, normal cells cultured with RET ligands survive almost three times better than with conventional medium (FIG. 3d-e; FIG. 10c).

RET signals determines HSC transplantation efficiency since foetal RET deficient cells have virtually no transplantation capacity (FIG. 2c). Remarkably, when transplanted in competition with normal cells, we could quantify transplantation efficiency. We found that RET deficient HSCs generate 10 times less cells in the blood and HSCs in the bone marrow (FIG. 2e-g). Strikingly adult bone marrow cells from RET deficient origin have almost 50 times less transplantation capacity than the normal cells in a secondary transplantation (FIG. 2h-j).

RET signals control HSC expansion in culture. In the presence of RET ligands HSC expansion is three times higher than with conventional medium only (FIG. 3d). Importantly, the RET treated expanded HSCs also have circa 300 fold increase in transplantation efficiency when compared to HSCs expanded in conventional medium (FIG. 4e-g). Together expansion and transplantation protocols that include RET agonists increase transplantation efficiency by almost 1000 fold in comparison to conventional medium.

The present embodiment can be applied in expansion and transplantation protocols of haematopoietic stem cells, to be used both in biomedical research and in clinical practice.

Supplementation of conventional culture conditions with RET agonists can be used to increase the number of cells recovered in expansion protocols. The use of HSCs in transplantation is severely constrained by the limited expansion of these cells: Current cell culturing techniques result in insufficient stem cell quantities; particularly if cord blood is used as a source. Compared with current conventional medium, which mildly expand haematopoietic progenitors but also cause differentiation, our formulation using RET agonist duplicate the number or cells recovered. In addition, RET agonist treatment do not alter the differentiation of cells, thus allowing three times more true HSCs to be recovered from expansion cultures (FIG. 3d). Most importantly, expanded HSCs with RET ligands have circa 300 fold increase in transplantation efficiency when compared to HSCs expanded in conventional conditions. Thus, the combined expansion and transplantation protocols including RET agonists increase transplantation efficiency by circa 1000 fold in comparison to conventional protocols.

Thus, activation of RET results in improved HSC survival/expansion and in vivo transplantation efficiency in mice. When compared to current state-of-the-art expansion methods, these experiments revealed that HSC expansion with neurotrophic factors result in a 20-fold increase of bona fide HSCs that maintain their stemness.

Altogether, our technology can significantly improve the expansion and thus the availability of HSCs for clinical and R&D use.

REFERENCES

[1] Trumpp, A., Essers, M. & Wilson, A. Awakening dormant haematopoietic stem cells. *Nat Rev Immunol* 10, 201-209 (2010).

[2] Yamazaki, S. et al. Nonmyelinating Schwann cells maintain hematopoietic stem cell hibernation in the bone marrow niche. *Cell* 147, 1146-1158 (2011).

3. Kondo, S., Kishi, H., Tokimitsu, Y. & Muraguchi, A. Possible involvement of glial cell line-derived neurotrophic factor and its receptor, GFRalpha1, in survival and maturation of thymocytes. *Eur J Immunol* 33, 2233-2240 (2003).
4. Vargas-Leal, V. et al. Expression and function of glial cell line-derived neurotrophic factor family ligands and their receptors on human immune cells. *J Immunol* 175, 2301-2308 (2005).
5. Veiga-Fernandes, H. et al. Tyrosine kinase receptor RET is a key regulator of Peyer's Patch organogenesis. *Nature* 446, 547-551 (2007).
6. Airaksinen, M. S. & Saarma, M. The GDNF family: signalling, biological functions and therapeutic value. *Nat Rev Neurosci* 3, 383-394 (2002).
7. Kiel, M. J., Yilmaz, O. H., Iwashita, T., Terhorst, C. & Morrison, S. J. SLAM family receptors distinguish hematopoietic stem and progenitor cells and reveal endothelial niches for stem cells. *Cell* 121, 1109-1121 (2005).
8. Kim, I., He, S., Yilmaz, O. H., Kiel, M. J. & Morrison, S. J. Enhanced purification of fetal liver hematopoietic stem cells using SLAM family receptors. *Blood* 108, 737-744 (2006).
9. Schuchardt, A., D'Agati, V., Larsson-Blomberg, L., Costantini, F. & Pachnis, V. Defects in the kidney and enteric nervous system of mice lacking the tyrosine kinase receptor Ret. *Nature* 367, 380-383 (1994).
10. Randall, T. D., Lund, F. E., Howard, M. C. & Weissman, I. L. Expression of murine CD38 defines a population of long-term reconstituting hematopoietic stem cells. *Blood* 87, 4057-4067 (1996).
11. de Boer, J. et al. Transgenic mice with hematopoietic and lymphoid specific expression of Cre. *Eur J Immunol* 33, 314-325 (2003).
12. Hock, H. et al. Gfi-1 restricts proliferation and preserves functional integrity of haematopoietic stem cells. *Nature* 431, 1002-1007 (2004).
13. Ohta, H. et al. Polycomb group gene rae28 is required for sustaining activity of hematopoietic stem cells. *J Exp Med* 195, 759-770 (2002).
14. Jankovic, V. et al. Id1 restrains myeloid commitment, maintaining the self-renewal capacity of hematopoietic stem cells. *Proc Natl Acad Sci USA* 104, 1260-1265 (2007).
15. Mansson, R. et al. Molecular evidence for hierarchical transcriptional lineage priming in fetal and adult stem cells and multipotent progenitors. *Immunity* 26, 407-419 (2007).
16. Terskikh, A. V., Miyamoto, T., Chang, C., Diatchenko, L. & Weissman, I. L. Gene expression analysis of purified hematopoietic stem cells and committed progenitors. *Blood* 102, 94-101 (2003).
17. Thompson, B. J. et al. Control of hematopoietic stem cell quiescence by the E3 ubiquitin ligase Fbw7. *J Exp Med* 205, 1395-1408 (2008).
18. Perianayagam, M. C., Madias, N. E., Pereira, B. J. & Jaber, B. L. CREB transcription factor modulates Bcl2 transcription in response to C5a in HL-60-derived neutrophils. *Eur J Clin Invest* 36, 353-361 (2006).
19. Shukla, A. et al. Activated cAMP response element binding protein is overexpressed in human mesotheliomas and inhibits apoptosis. *Am J Pathol* 175, 2197-2206 (2009).
20. Smith-Hicks, C. L., Sizer, K. C., Powers, J. F., Tischler, A. S. & Costantini, F. C-cell hyperplasia, pheochromocytoma and sympathoadrenal malformation in a mouse model of multiple endocrine neoplasia type 2B. *Embo J* 19, 612-622 (2000).
21. Nakayama, K., Negishi, I., Kuida, K., Sawa, H. & Loh, D. Y. Targeted disruption of Bcl-2 alpha beta in mice: occurrence of gray hair, polycystic kidney disease, and lymphocytopenia. *Proc Natl Acad Sci USA* 91, 3700-3704 (1994).
22. Cacalano, G. et al. GFRalpha1 is an essential receptor component for GDNF in the developing nervous system and kidney. *Neuron* 21, 53-62 (1998).
23. Nishino, J. et al. GFR alpha3, a component of the artemin receptor, is required for migration and survival of the superior cervical ganglion. *Neuron* 23, 725-736 (1999).
24. Rossi, J. et al. Retarded growth and deficits in the enteric and parasympathetic nervous system in mice lacking GFR alpha2, a functional neurturin receptor. *Neuron* 22, 243-252 (1999).
25. Patel, A. et al. Differential RET signaling responses orchestrate lymphoid and nervous enteric system development. *Science Signaling* (in press) (2012).
26. Katayama, Y. et al. Signals from the sympathetic nervous system regulate hematopoietic stem cell egress from bone marrow. *Cell* 124, 407-421 (2006).
27. Spiegel, A. et al. Catecholaminergic neurotransmitters regulate migration and repopulation of immature human CD34+ cells through Wnt signaling. *Nat Immunol* 8, 1123-1131 (2007).
28. Mendez-Ferrer, S. et al. Mesenchymal and haematopoietic stem cells form a unique bone marrow niche. *Nature* 466, 829-834 (2010).
29. Mombaerts, P. et al. RAG-1-deficient mice have no mature B and T lymphocytes. *Cell* 68, 869-877. (1992).
30. Peixoto, A., Monteiro, M., Rocha, B. & Veiga-Fernandes, H. Quantification of multiple gene expression in individual cells. *Genome Res* 14, 1938-1947 (2004).

The invention claimed is:
1. A method for regulating hematopoietic stem cell survival, maintenance, expansion or transplantation in connection with a hematopoietic stem cell maintenance or expansion protocol or transplantation therapy, which comprises
contacting a population of hematopoietic stem cells in-vitro with an agonist of the glial derived neurotrophic factor (GDNF) family of ligands under conditions such that the hematopoietic stem cells maintain their stemness so as to obtain survival, maintenance or expansion of the population of hematopoietic stem cells or for transplantation through the administration into a subject in need thereof the population of hematopoietic stem cells contacted with the agonist of the GDNF family of ligands.
2. A method for the treatment of any condition susceptible of being improved or prevented by hematopoietic stem cell transplantation therapy in a subject in need thereof, which comprises
contacting a population of hematopoietic stem cells in-vitro with an agonist of the GDNF family of ligands under conditions such that the hematopoietic stem cells maintain their stemness so as to obtain survival, maintenance or expansion of the population of hematopoietic stem cells or for transplantation through the administration into the subject in need thereof the population of hematopoietic stem cells contacted with the agonist of the GNDF family of ligands.

* * * * *